United States Patent [19]

Shimazaki et al.

[11] Patent Number: 4,940,709
[45] Date of Patent: * Jul. 10, 1990

[54] PIPERAZINE COMPOUND AS PAF-ANTAGONIST

[75] Inventors: Norihiko Shimazaki; Keiji Hemmi, both of Ibaraki; Osamu Nakaguti, Toyonaka; Yoshio Miyazaki, Itami; Masashi Hashimoto, Ibaraki, all of Japan

[73] Assignee: Fujisawa Pharmaceutical Co., Ltd., Osaka, Japan

[*] Notice: The portion of the term of this patent subsequent to Feb. 21, 2006 has been disclaimed.

[21] Appl. No.: 123,324

[22] Filed: Nov. 20, 1987

Related U.S. Application Data

[63] Continuation-in-part of Ser. No. 31,577, Mar. 30, 1987, Pat. No. 4,806,538, which is a continuation of Ser. No. 790,082, Oct. 22, 1985, abandoned.

[30] Foreign Application Priority Data

Nov. 2, 1984 [GB] United Kingdom ............... 8427735
Apr. 23, 1986 [GB] United Kingdom ............... 8609908
Dec. 31, 1986 [GB] United Kingdom ............... 8631082

[51] Int. Cl.⁵ ............... A61K 31/495; C07D 241/08
[52] U.S. Cl. ............... 514/253; 514/252; 514/255; 544/360; 544/363; 544/364; 544/367; 544/368; 544/369; 544/373; 544/376; 544/380; 544/385
[58] Field of Search ............... 544/360, 368, 369, 373, 544/381, 385, 363, 364, 367, 385, 376; 514/252, 253, 255

[56] References Cited

U.S. PATENT DOCUMENTS

| | | | |
|---|---|---|---|
| 3,976,773 | 8/1976 | Curran | 544/385 |
| 4,038,429 | 7/1977 | Smith et al. | 544/385 |
| 4,111,925 | 9/1978 | Bachman | 562/450 |
| 4,289,707 | 9/1981 | Caldwell et al. | 544/385 |
| 4,289,759 | 9/1981 | Heavner et al. | 544/385 |
| 4,554,102 | 11/1985 | Dong et al. | 558/351 |
| 4,569,793 | 2/1986 | Dong et al. | 558/351 |
| 4,611,076 | 9/1986 | Dong et al. | 558/351 |
| 4,694,081 | 9/1987 | Miller et al. | 544/385 |

FOREIGN PATENT DOCUMENTS

| | | | |
|---|---|---|---|
| 181152 | 5/1986 | European Pat. Off. | |
| 216744 | 4/1987 | European Pat. Off. | 544/385 |
| 216746 | 4/1987 | European Pat. Off. | 544/385 |
| 2215408 | 11/1972 | Fed. Rep. of Germany | 544/385 |
| 6002969 | 1/1981 | Japan | 544/385 |
| 1600127 | 10/1981 | United Kingdom | |

OTHER PUBLICATIONS

Tran et al, Chem. Abst., 96-218218f (1982).
Hope et al, Chem. Abst., 86-16936w, "The Application of Ketimine Derivatives of Amino Acids to Peptide Synthesis".
Sumitomo Chemical Co. Ltd., JP 5913779, Chem. Abst. 100-209873q (1984).
Johne et al, Die Pharmazie, vol. 32, No. 1 (1977), pp. 1-16.
Kanmera et al, Chem. Abst. 95-7743q (1981).
Kanmera et al, Chem. Abst. 93-221027m (1980).
Hashimoto et al, Chem. Abst. 98-215972c.

*Primary Examiner*—Cecilia Shen
*Attorney, Agent, or Firm*—Oblon, Spivak, McClelland, Maier & Neustadt

[57] ABSTRACT

Diseases caused by platelet activating factor are prevented and treated by administration to a subject of a therapeutically effective amount of a piperazine compound of the formula:

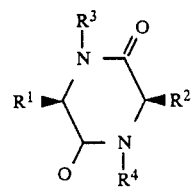

wherein $R^1$ to $R^4$ are as defined in the specification.

1 Claim, No Drawings

PIPERAZINE COMPOUND AS PAF-ANTAGONIST

This invention relates to new PAF (Platelet Activating Factor) antagonists, piperazine compounds (I) and pharmaceutically acceptable salt thereof. More particularly, it relates to a pharmaceutical composition comprising the piperazine compounds (I) or pharmaceutically acceptable salt thereof as an active ingredient, and to a new piperazine compound (Ia) and pharmaceutically acceptable salt thereof and to processes for the preparation thereof.

This invention based on new discovery by the present inventors that certain piperazine compounds (I) and pharmaceutically acceptable salt thereof are highly potent antagonists of PAF and therefore useful for the prevention and treatment of diseases caused by PAF.

The piperazine compounds of this invention can be represented by the following formula:

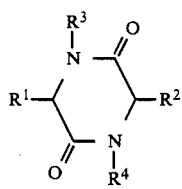
(I)

wherein
$R^1$ is aryl;
  ar(lower)alkyl which may have lower alkoxy;
  heterocyclic(lower)alkyl which may have substituent(s) selected from the group of lower alkyl and aryl on the heterocyclic ring; or
  a group of the formula:

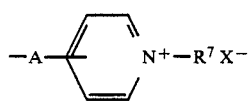

wherein
  A is lower alkylene,
  $R^7$ is lower alkyl and
  X is acid residue;
$R^2$ is
  lower alkyl;
  higher alkyl;
  lower alkylthio(lower)alkyl;
  lower alkenylthio(lower)alkyl;
  hydroxy(lower)alkyl;
  protected hydroxy(lower)alkyl;
  amino(lower)alkyl;
  protected amino(lower)alkyl;
  carboxy(lower)alkyl;
  protected carboxy(lower)alkyl;
  arylthio(lower)alkyl;
  ar(lower)alkylthio(lower)alkyl;
  heterocyclic(lower)alkyl which may have substituent(s) selected from the group of lower alkyl, halogen, lower alkoxy, aryl and ar(lower)alkoxy on the heterocyclic ring; or
  heterocyclic-substituted ar(lower)alkyl which may have lower alkyl on the herocyclic ring; and
$R^3$ and $R^4$ are each hydrogen or lower alkyl.

The piperazine compounds (I) include known and novel compounds.

Among the piperazine compound (I), the new and preferred stereochemically specific compound can be represented by the following formula:

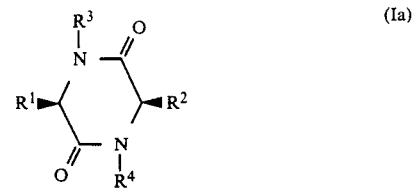
(Ia)

wherein $R^1$, $R^2$, $R^3$ and $R^4$ are each as defined above.

The pharmaceutically acceptable salt of the compound (I) and (Ia) may include an organic or inorganic acid addition salt (e.g. hydrochloride, etc.) and a salt with an organic or inorganic base (e.g. sodium salt, etc.).

According to this invention, the piperazine compounds (I) and pharmaceutically acceptable salt thereof can be prepared by, for example, the following processes.

Process 1:

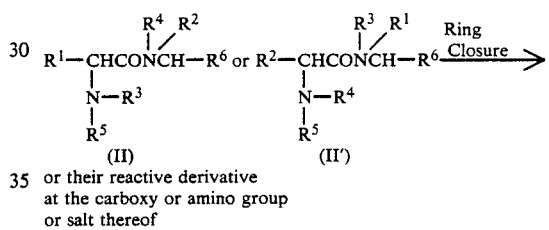

or their reactive derivative
at the carboxy or amino group
or salt thereof

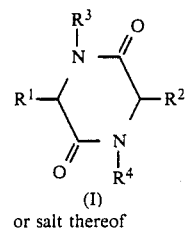

(I)
or salt thereof

Process 2:

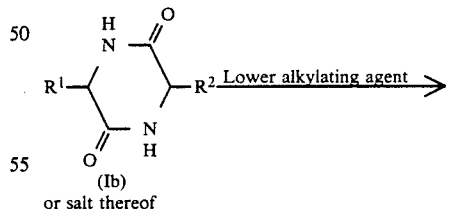

(Ib)
or salt thereof

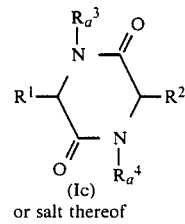

(Ic)
or salt thereof

Process 3:

-continued

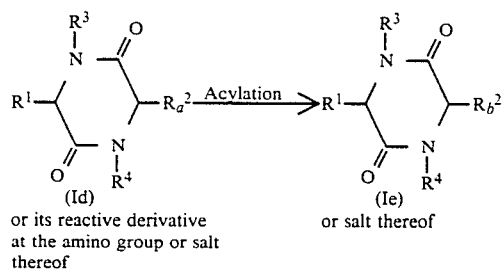
(Id) or its reactive derivative at the amino group or salt thereof → (Ie) or salt thereof Process 4:

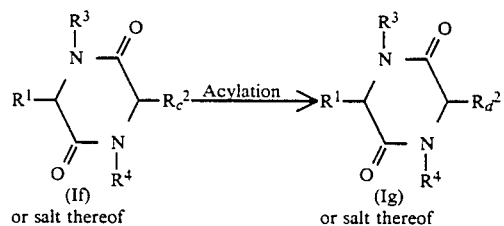
(If) or salt thereof → (Ig) or salt thereof

Process 5:

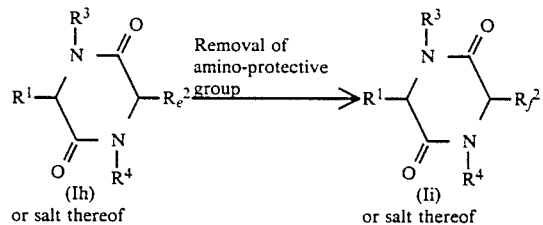
(Ih) or salt thereof → (Ii) or salt thereof

Process 6:

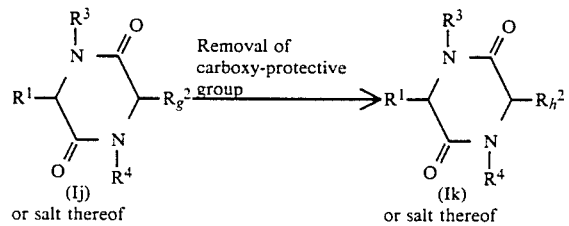
(Ij) or salt thereof → (Ik) or salt thereof

Process 7:

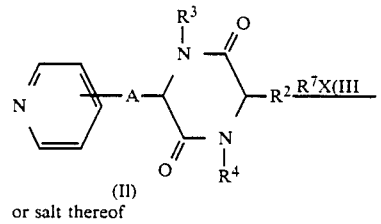
(II) or salt thereof

Process 8:

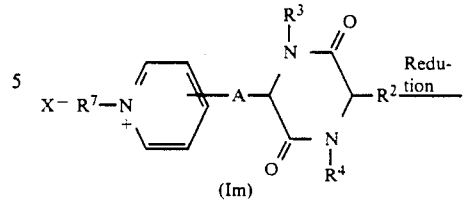
(Im)

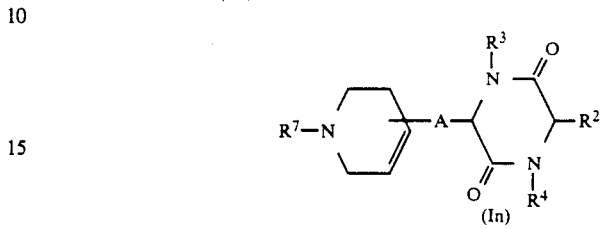
(In)

wherein
$R^1$, $R^2$, $R^3$ and $R^4$ are each as defined above,
$R_a^2$ and $R_f^2$ are each amino(lower)alkyl,
$R_b^2$ is acylamino(lower)alkyl,
$R_c^2$ is hydroxy(lower)alkyl,
$R_d^2$ is acyloxy(lower)alkyl,
$R_e^2$ is a protected amino(lower)alkyl,
$R_g^2$ is a protected carboxy(lower)alkyl,
$R_h^2$ is carboxy(lower)alkyl,
$R_a^3$ and $R_a^4$ are each lower alkyl, $R^5$ is hydrogen or amino-protective group $R^6$ is carboxy or a protected carboxy,
A is lower alkylene,
$R^7$ is lower alkyl and
X is acid residue.

The starting compounds (II) and (II') include known compounds and new ones and can be prepared by subjecting the corresponding two amino acids to peptide linkage formation reaction in a conventional manner.

In the above and subsequent descriptions of this specification, suitable examples and illustrations of the various definitions are explained in detail in the followings.

The term "lower" is intended to mean 1 to 6 carbon atom(s), unless otherwise indicated.

The term "higher" is intended to mean more than 6 carbon atoms, preferably 7 to 22 carbon atoms and more preferably 7 to 18 carbon atoms.

Suitable "aryl" group and "aryl" moiety in the term "arylthio(lower)alkyl" may include phenyl, tolyl, naphthyl, anthryl, phenanthryl and the like.

Suitable "ar(lower)alkyl" group and "ar(lower)alkyl" moiety in the term "ar(lower)alkylthio(lower)alkyl" and "heterocyclic-substituted ar(lower)alkyl" may include mono(or di or tri)phenyl(lower)alkyl (e.g. benzyl, phenethyl, benzhydryl, trityl, 1-phenylethyl etc.) naphthyl(lower)alkyl (e.g. naphthylmethyl, 1-naphthylethyl, etc.), anthryl(lower)alkyl (e.g. anthrylmethyl, etc.), phenanthryl(lower)alkyl (e.g. phenanthrylmethyl, etc.) and the like.

Suitable "lower alkoxy" may include methoxy, ethoxy, propoxy, isopropoxy, butoxy, isobutoxy, sec-butoxy, tert-butoxy, pentyloxy, hexyloxy and the like.

Suitable "lower alkyl" group and "lower alkyl" moiety in the terms "heterocyclic(lower)alkyl", "lower alkylthio(lower)alkyl", "hydroxy(lower)alkyl", "protected hydroxy(lower)alkyl", "amino(lower)alkyl", "protected amino(lower)alkyl", "carboxy(lower)alkyl", "protected carboxy(lower)alkyl", "arylthio(lower)alkyl", "ar(lower)alkylthio(lower)alkyl" and "acyloxy(lower)alkyl" may include methyl, ethyl, propyl, isopropyl, butyl, isobutyl, sec-butyl, tert-butyl, pentyl, hexyl and the like.

Suitable "heterocyclic" moiety in the terms "heterocyclic(lower)alkyl" and "heterocyclic-substituted ar(lower)alkyl" may include benzene-fused heterocyclic group containing at least one hetero-atom such as oxygen, sulfur and nitrogen (e.g. indolyl, benzothienyl, quinolyl, etc.), heteromonocyclic group containing at least one hetero-atom such as oxygen, sulfur and nitrogen (e.g. pyridyl, tetrahydropyridyl, thiazolyl, etc.), and the like.

Suitable "higher alkyl" may include heptyl, octyl, decyl, dodecyl, tetradecyl, hexadecyl, octadecyl and the like.

Suitable "lower alkenyl" moiety in the term "lower alkenylthio(lower)alkyl" may include lower alkenyl having 2 to 6 carbon atoms such as vinyl, allyl, isopropenyl, 2-butenyl, 3-pentenyl, 4-hexenyl and the like.

Suitable "protected hydroxy" group may include acyloxy such as lower alkanoyloxy (e.g. acetoxy, propionyloxy, etc.) ant the like, ar(lower)alkoxy such as mono(or di or tri)phenyl(lower)alkoxy (e.g. benzyloxy, etc.) and the like.

The "amino-protective group" and "amino-protective" moiety in the term "protected amino" include a conventional amino-protective group which is used in the field of amino acid and peptide chemistry, and suitable "amino-protective group" may include acyl such as lower alkanoyl (e.g. formyl, acetyl, propionyl, etc.), aroyl (e.g. benzoyl, etc.), lower alkoxycarbonyl (e.g. methoxycarbonyl, ethoxycarbonyl, propoxycarbonyl, etc.), ar(lower)alkoxycarbonyl [e.g. mono(or di or tri)phenyl(lower)alkoxycarbonyl (e.g. benzyloxycarbonyl, etc.), etc.] and the like.

Suitable "protected carboxy" may include esterified carboxy such as lower alkoxycarbonyl as aforementioned, ar(lower)alkoxycarbonyl as aforementioned, and the like.

Suitable "ar(lower)alkoxy" may include mono(or di or tri)phenyl(lower)alkoxy (e.g. benzyloxy, phenethyloxy, benzhydryloxy, trityloxy, etc.) and the like.

The term "halogen" may include fluorine, chlorine, bromine, iodine and the like.

Suitable "lower alkylene" may include methylene, methylmethylene, ethylene, trimethylene, tetramethylene, pentamethylene, hexamethylene and the like.

Suitable "acid residue" may include halogen as exemplified above.

Preferable embodiments of the object compound (I) are as follows.

Preferable embodiment of $R^1$ is aryl (more preferably phenyl); ar(lower)alkyl [more preferably mono(or di)phenyl(lower)alkyl, naphthyl(lower)alkyl or anthryl(lower)alkyl]; ar(lower)alkyl having lower alkoxy [more preferably phenyl(lower)alkyl having lower alkoxy]; heterocyclic(lower)alkyl [more preferably benzene-fused heterocyclic(lower)alkyl containing one sulfur or nitrogen atom [most preferably, indolyl(lower)alkyl or benzothienyl(lower)alkyl or quinolyl(lower)alkyl]; heteromonocyclic(lower)alkyl containing one nitrogen atom [most preferably pyridyl(lower)alkyl]; heteromonocyclic(lower)alkyl containing one nitrogen atom and one sulfur atom [most preferably thiazolyl(lower)alkyl]; heterocyclic(lower)alkyl having lower alkyl on the heterocyclic ring [more preferably N-lower alkyl-benzene-fused heterocyclic(lower)alkyl containing one nitrogen atom [most preferably N-lower alkylindolyl(lower)alkyl] or N-lower alkyl-heteromonocyclic(lower)alkyl containing one nitrogen atom [most preferably N-lower alkyltetrahydropyridyl(lower)alkyl]]; or heterocyclic(lower)alkyl having lower alkyl and aryl on the heterocyclic ring [more preferably N-lower alkyl-benzene-fused heterocyclic(lower)alkyl containing one nitrogen atom having aryl on the heterocyclic ring [most preferably N-lower alkylindolyl(lower)alkyl having phenyl on the indole ring]]; or a group of the formula:

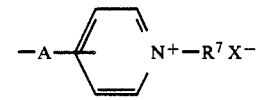

wherein A is lower alkylene, $R^7$ is lower alkyl and X is acid residue (more preferably halogen); $R^2$ is lower alkyl; higher alkyl; lower alkylthio(lower)alkyl; lower alkenylthio(lower)alkyl; hydroxy(lower)alkyl; protected hydroxy(lower)alkyl [more preferably acyloxy(lower)alkyl [most preferably lower alkanoyloxy(lower)alkyl] and ar(lower)alkoxy(lower)alkyl [most preferably phenyl(lower)alkoxy(lower)alkyl]; amino(lower)alkyl; protected amino(lower)alkyl [more preferably acylamino(lower)alkyl [most preferably lower alkanoylamino(lower)alkyl, benzamido(lower)alkyl, lower alkoxycarbonylamino(lower)alkyl or phenyl(lower)alkoxycarbonylamino(lower)alkyl]]; carboxy(lower)alkyl; protected carboxy(lower)alkyl [more preferably esterified carboxy(lower)alkyl [most preferably lower alkoxycarbonyl(lower)alkyl or phenyl(lower)alkoxycarbonyl(lower)alkyl]]; arylthio(lower)alkyl [more preferably phenylthio(lower)alkyl]; ar(lower)alkylthio(lower)alkyl [more preferably phenyl(lower)alkylthio(lower)alkyl]; or heterocyclic(lower)alkyl having substituent(s) selected from the group of lower alkyl, halogen, lower alkoxy, aryl and ar(lower)alkoxy on the heterocyclic ring [more preferably, N-lower alkyl-benzene-fused heterocyclic(lower)alkyl containing one nitrogen atom [most preferably N-lower alkylindolyl(lower)alkyl], N-lower alkyl-benzene-fused heterocyclic(lower)alkyl containing one nitrogen atom having lower alkyl(s) on the heterocyclic ring [most preferably N-lower alkylindolyl(lower)alkyl having one or two lower alkyl(s) on the indole ring], N-lower alkyl-benzene-fused heterocyclic(lower)alkyl containing one nitrogen atom having halogen on the heterocyclic ring [most preferably N-lower alkylindolyl(lower)alkyl having halogen on the indole ring], N-lower alkyl-benzene-fused heterocyclic(lower)alkyl containing one nitrogen atom having lower alkyl and halogen on the heterocyclic ring [most preferably N-lower alkylindolyl(lower)alkyl having lower alkyl and halogen on the indole ring], N-lower alkyl-benzene-fused heterocyclic(lower)alkyl containing one nitrogen atom having lower alkoxy on the heterocyclic ring [most preferably N-lower alkylindolyl(lower)alkyl having lower alkoxy on the indole ring], N-lower alkyl-benzene-fused heterocyclic(lower)alkyl containing one nitrogen atom having aryl on the heterocyclic ring [most preferably N-lower alkylindolyl(lower)alkyl having phenyl on the indole ring], or N-lower alkyl-benzene-fused heterocyclic(lower)alkyl containing one nitrogen atom having ar(lower)alkoxy on the heterocyclic ring [most preferably N-lower alkylindolyl(lower)alkyl having phenyl(lower)alkoxy on the indole ring]]; or N-lower alkyl-benzenefused heterocyclic containing one nitrogen atom- and aryl-disubstituted lower alkyl [most preferably N-lower alkyl indolyl- and phenyl-disubstituted lower alkyl] and $R^3$ and $R^4$ are each hydrogen or lower alkyl.

The salts of the compounds (Ib), (Ic), (Id), (Ie), (If), (Ig), (Ih), (Ii), (Ij), (Ik), (II) and (II') are substantially the same salt as those exemplified in the explanation of the pharmaceutically acceptable salt of the compound (I).

The process as illustrated above are explained in more detail in the followings.

Process 1

The object compound (I) or salt thereof can be prepared by subjecting the compound (II) or (II') or their reactive derivative at the carboxy or amino group or salt thereof to ring closure reaction.

Suitable reactive derivative at the amino group of compounds (II) and (II') may include Schiff's base type imino or its tautomeric enamine type isomer formed by the reaction of the compounds (II) or (II') with a carbonyl compound such as aldehyde, ketone or the like; a silyl derivative formed by the reaction of the compounds (II) or (II') with a silyl compound such as bis(-trimethylsilyl)acetamide, trimethylsilylacetamide or the like.

The suitable reactive derivative at the carboxy of compounds (II) or (II') may be a conventional one such as an acid halide (e.g. acid chloride, acid bromide, etc.), an acid azide, an acid anhydride, an activated amide, an activated ester and the like.

When free acid is used as the starting compounds (II) and (II'), the reaction may preferably be conducted in the presence of a conventional condensing agent.

The reaction can also be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,-0]undecene-5, etc.) and the like.

This reaction is usually carried out without solvent or in the presence of a solvent which does not adversely influence the reaction such as methanol, ethanol, propanol, acetic acid, dimethylformamide, dichloroethane, toluene, benzene, xylene and the like.

The reaction temperature is not critical, and the reaction is usually carried out under heating to under cooling.

When the compound (II) or (II') having amino-protective group for $R^5$ is used as a starting compound, it may often give preferred results to remove the amino-protective group in a conventional manner (e.g. hydrolysis, catalytic reduction, etc.) prior to this ring closure reaction.

Process 2:

The object compound (Ic) or salt thereof can be prepared by reacting the compound (Ib) or salt thereof with a lower alkylating agent.

The lower alkylating agent may include lower alkyl halide (e.g. methyl iodide, etc.), di(lower)alkylsulfate (e.g. dimethylsulfate, etc.), diazo(lower)alkane (e.g. diazomethane, etc.), lower alkyl sulfonate (e.g. methyl sulfonate, etc.) and the like.

This reaction can be conducted in the presence of an organic or inorganic base as those exemplified in the explanation of Process 1.

This reaction is usually carried out in the presence of a solvent which does not adversely influence the reaction such as dichloromethane, dimethylformamide and the like.

The reaction temperature is not critical and the reaction is sufficiently carried out at ambient temperature.

Process 3:

The object compound (Ie) or salt thereof can be prepared by reacting the compound (Id) or its reactive derivative at the amino group or salt thereof with an acylating agent.

Suitable reactive derivative at the amono group of the compound (Id) is substantially the same as that of the compound (II) explained in the Process 1.

The acylating agent to be used in this reaction includes an organic acid (i.e. $R^7$ OH (IV), in which $R^7$ is acyl) and its reactive derivative.

The suitable reactive derivative of the compound (IV) is substantially the same as that of the compound (II) explained in Process 1.

When free acid is used as an acylating agent, the acylation reaction may preferably be conducted in the presence of a conventional condensing agent.

The reaction can preferably be conducted in the presence of an organic or inorganic base as those exemplified in the explanation of the above Process 1.

This reaction is usually carried out in a solvent which does not adversely influence the reaction such as methanol, ethanol, propanol, tetrahydrofuran, chloroform, pyridine and the like.

The reaction temperature is not critical and the reaction can be carried out under heating to under cooling.

Process 4:

The compound (Ig) or salt thereof can be prepared by reacting the compound (If) or salt thereof with an acylating agent.

The reaction conditions and the acylating agent are substantially the same as those explained in the Process 3.

Process 5:

The compound (Ii) or salt thereof can be prepared by subjecting the compound (Ih) or salt thereof to removal reaction of amino-protective group.

The removal reaction of this process is carried out in a conventional manner (e.g. hydrolysis, catalytic reduction, reduction, etc.).

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The catalytic reduction can be carried out in the presence of a conventional catalyst for catalytic reduction (e.g. paradium on charcoal, etc.) at atmospheric pressure.

The reaction of this process is usually carried out in a solvent which does not adversely influence the reaction such as methanol, ethanol, propanol, acetic acid and the like, at a temperature range of cooling to heating.

Process 6:

The compound (Ik) or salt thereof can be prepared by subjecting the compound (Ij) or salt thereof to removal reaction of the carboxy-protective group.

The removal reaction is carried out in substantially the same manner as that of Process 5.

Process 7:

The compound (Im) can be prepared by reacting the compound (Il) or salt thereof with the compound (III).

This reaction is usually carried out without solvent or in the presence of a solvent which does not adversely influence the reaction such as methanol, ethanol, propanol, acetic acid, dimethylformamide, dichloroethane, toluene, benzene, xylene and the like.

The reaction temperature is not critical, and the reaction is usually carried out under heating to under cooling.

Process 8:

The compound (In) can be prepared by reducing the compound (Im).

In the reduction, there may usually be employed a reducing agent such as alkali metal borohydride (e.g. sodium borohydride, etc.) and the like.

This reaction is usually carried out in a solvent which does not adversely influence the reaction such as methanol, ethanol, propanol, acetic acid, dimethylformamide, dichloroethane, toluene, benzene, xylene and the like.

The reaction temperature is not critical, and the reaction is usually carried out under heating to under cooling.

The object compounds (I), (Ic), (Ie), (Ig), (Ii), (Ik), (Im) and (In) in the above processes can be purified and converted to the desired salts in a conventional manner.

The object compounds (I) and pharmaceutically acceptable salt thereof are antagonists of PAF and therefore useful as a medicine for preventing and treating diseases caused by PAF such as allergic manifestation (e.g. asthma, etc.), thrombosis, nephritis, endotoxin shock (ARDS), and the like.

The following Tests are given for the purpose of illustrating antagonism of the compounds (I) against PAF.

The test compounds are listed below.

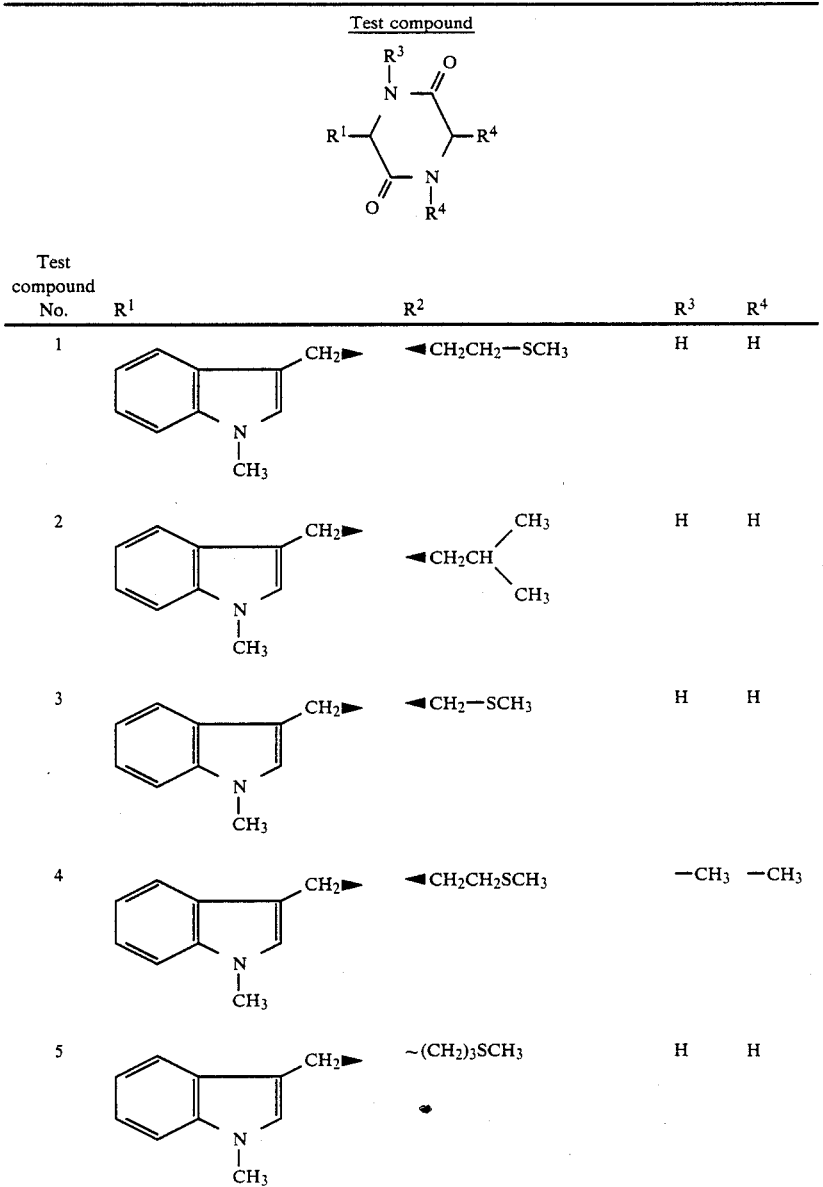

-continued
Test compound
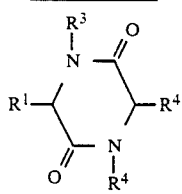
| Test compound No. | R¹ | R² | R³ | R⁴ |
|---|---|---|---|---|
| 6 | (C₆H₅)₂CH– | –CH₂CH₂SCH₃ | H | H |
| 7 | (1-methylindol-3-yl)-CH₂– | –CH₂-(1-methylindol-3-yl) | H | H |
| 8 | (1-methylindol-3-yl)-CH₂– | –(CH₂)₃CH₃ | H | H |
| 9 | (1-naphthyl)-CH(CH₃)– | –CH₂CH₂SCH₃ | H | H |
| 10 | (1-naphthyl)-CH₂– | –CH₂CH₂SCH₃ | H | H |
| 11 | (9-anthryl)-CH₂– | –CH₂CH₂SCH₃ | H | H |
| 12 | (1-naphthyl)-CH(CH₃)– | –CH₂CH₂SCH₃ | H | H |

-continued

Test compound

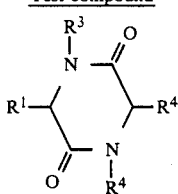

| Test compound No. | R¹ | R² | R³ | R⁴ |
|---|---|---|---|---|
| 13 | 3-CH₂- of 1-methyl-2-phenylindole | CH₂CH₂SCH₃ | H° | H |
| 14 | 3-CH₂- of 1-methylindole | CH₂CH₂CH₃ | H | H |
| 15 | C₆H₅-CH₂- | CH₂- of 1-methylindol-3-yl | H | H |
| 16 | 1-(1-naphthyl)ethyl (H, CH₃) | CH₂CH₂SCH₃ | —CH₃ | —CH₃ |
| 17 | 1-(1-naphthyl)ethyl (H, CH₃) | (CH₂)₃CH₃ | —CH₃ | —CH₃ |
| 18 | 1-(1-methylindol-3-yl)ethyl (H, CH₃) | CH₂- of 2-pyridyl | H | H |
| 19 | 1-(5-chloro-1-ethylindol-3-yl)ethyl (H, CH₃) | CH₂- of 2-pyridyl | H | H |

TEST 1 (Inhibition of platelet aggregation)

Test Method

Blood was collected through the polyethylene catheter introduced into the carotid artery of male Japanese white rabbit (2.5 to 3 kg body weight). The blood was anticoagulated with 1 volume of 3.8% sodium citrate at 9 volume of blood. Platelet rich plasma (PRP) was prepared by centrifugation of the blood at 150 g for 10 minutes at room temperature. The PRP was diluted with platelet poor plasma obtained by further centrifugation of the blood at 1,000 g for 20 minutes. The platelet number was $5 \times 10^5$ cells/mm$^3$. Platelet aggregation induced with PAF was measured by the nephelometric technique of Born and Cross [cf. Journal of Physiology 168, 178–188 (1963)] using HKK Hema tracer (trade name, made by Niko Bioscience Inc.).

Activities of inhibitors were expressed as IC$_{50}$ value, i.e. concentrations required to inhibit the platelet aggregation response by 50%. The final concentration of PAF was usually 20 nM. The test results are shown in the following table.

| Test compound No. | Test result IC$_{50}$ (μg/ml) |
|---|---|
| 1 | 0.71 |
| 2 | 1.04 |
| 3 | 2.5 |
| 4 | 0.84 |
| 5 | 0.55 |
| 6 | 0.75 |
| 7 | 1.2 |
| 8 | 0.58 |
| 9 | 0.061 |
| 10 | 0.48 |
| 11 | 0.58 |
| 12 | 0.65 |
| 13 | 0.72 |
| 14 | 0.93 |
| 15 | 0.82 |
| 16 | 0.59 |
| 17 | 0.55 |
| 18 | 0.16 |
| 19 | 0.015 |

TEST 2 (Inhibition of hypotensive effect induced by intraveneously injected PAF in rats)

Test Method

Seven-week old Sprague-Dowley rats were anesthetized with urethane (1 g/kg, i. p.). Catheters were introduced into the femoral artery and vein for the measurement of arterial pressure and the administration of the test compound, respectively. Blood pressure was recorded from femoral artery using a transducer coupled to the Biophysiograph 180 System (San-Ei Instrument Co., Ltd.). Inhibitory activity of the test compound was shown in the following Table as the inhibition percentage of the synthetic PAF induced hypotension. PAF was administered intravenously at a dose of 1 μg/kg. The test compound was administered intravenously 3 minutes before PAF injection.

| Test compound No. | Dose (mg/kg) | Test result Inhibition maximum (%) of hypotensive effect |
|---|---|---|
| 2 | 10 | 75 |
| 9 | 3 | 51 |
| 18 | 10 | 72 |

TEST 3 (Inhibition of vascular permeability increase induced by intradermally injected PAF in mice)

Test Method

Six-week old male ddY mice were used. The test compound was administered intraperitoneally 15 minutes before the Evans blue injection (0.125% solution in saline, 0.2 ml/mouse, i.v.).

PAF (50 ng, 50 μl per site) was injected intradermally to the depilated back of the mice 5 minutes after the Evans blue injection.

The inhibitory activity of the test compound was monitored 30 minutes after the PAF injection by assessment of blueing reaction with Evans blue dye in mice skin.

The test results are shown in the following table.

| Test compound No | Dose (mg/kg) | Inhibition of vascular permeability increase (%) |
|---|---|---|
| 2 | 10 | 30 |
| 9 | 10 | 40 |
| 18 | 1 | 35 |

TEST 4 (Inhibition of vascular permeability increase induced by intradermally injected PAF in mice)

Test Method

Five-week old male ddY mice were used. The test compound suspended in 0.5 methylcellulose suspension was administered orally 30 minutes before the Evans blue injection (0.125% solution in saline, 10 ml/kg, i.v.).

PAF (50 ng, 50 μl per site) was injected intradermally to the depilated back of the mice 5 minutes after the Evans blue injection.

The inhibitory activity of the test compound was monitored 30 minutes after the PAF injection by assessment of blueing reaction with Evans blue dye in mice skin.

| Test compound No | Dose (mg/kg) | Test result Inhibition of vascular permeability increase (%) |
|---|---|---|
| 18 | 100 | 56.7 |

The compounds (I) or pharmaceutically acceptable salt thereof in admixture with pharmaceutically acceptable carriers can be administered orally or parenterally to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of glycyrrhizin, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. surface active agent, etc.], aqueous diluting agent (e.g. water), base wax (e.g. cacao butter, polyethyleneglycol, white petrolatum, etc.).

A dosage of the object compounds is to be varied depending on various factors such as kind of diseases, weight and/or age of a patient, and further the kind of administration route.

The optimal dosage of the compounds (I) is usually selected from a dose range of 1 mg–1 g/day, preferably 10 mg—500 mg/day.

The total daily amount mentioned above may be divisionally given to the patient at the interval of 6–12 hours per day.

The following Examples are given for the purpose of illustrating this invention.

EXAMPLE 1

(1) To a suspension of N-tert-butoxycarbonyl-1-methyl-D-tryptophan (1.60 g) and hydrochloric acid salt of D-methionine ethyl ester (1.06 g) in dry methylene chloride (30 ml) which was cooled on an ice bath and stirred was added a solution of triethylamine (0.50 g) in dry methylene chloride (10 ml). The mixture was stirred for 30 minutes, and to the mixture was added a solution of N,N'-dichlorohexylcarbodiimide (1.04 g) in dry methylene chloride (10 ml). The resulting mixture was stirred overnight. After removal of the solvent, crude residue was taken up with a mixture of ethyl acetate and water, filtered, and organic layer was washed with 10% hydrochloric acid and saturated sodium bicarbonate solution, dried over magnesium sulfate, and evaporated to give crystalline N-tert-butoxycarbonyl-1-methyl-D-tryptophyl-D-methionione ethyl ester (2.43 g).

NMR (CDCl$_3$) δ: 1.21 (3H, t, J=7 Hz), 1.36 (9H, s), 1.95 (2H, m), 1.97 (3H, s), 2.25 (2H, m), 3.13 (1H, dd, J=14 Hz, 7 Hz), 3.35 (1H, dd, J=14 Hz, 6 Hz), 3.73 (3H, s), 4.14 (2H, q, J=7 Hz), 4.50 (2H, m), 5.12(1H, d, J=7 Hz, 6.50 (1H, d, J=7 Hz), 6.95 (1H, s), 7.25 (3H, m), 7.66 (1H, m).

(2) A mixture of N-tert-butoxycarbonyl-1-methyl-D-tryptophyl-D-methionine ethyl ester (2.4 g), formic acid (25 ml), and saturated solution of hydrogen chloride in formic acid (10 ml) was stirred on an ice bath for 1.5 hours. After removal of the solvent, the crude residue was dissolved in ethanol (20 ml) and saturated ammonia in ethanol (10 ml) was added. The resulting mixture was stirred for 16 hours at room temperature and precipitated mass was collected, washed with ethanol, and dried. Recrystallization from ethanol gave (3R,6R)-3-(1-methylindol-3-ylmethyl)-6-(2-methylthioethyl)piperazine-2,5-dione (1.16 g).

mp: 229°–231° C.

IR (Nujol): 1165 cm$^{-1}$.

NMR (DMSO-d$_6$) δ: 1.05 (2H, m), 1.50 (2H, m), 1.65 (3H, s), 2.90 (1H, dd, J=14 Hz, 5 Hz), 3.25 (1H, dd, J=14 Hz, 5 Hz), 3.62 (1H, m), 3.67 (3H, s), 4.08 (1H, m), 6.98 (1H, s), 7.00 (2H, m), 7.30 (1H, dd, J=7 Hz, 2 Hz), 7.59 (1H, dd, J=7 Hz, 2 Hz), 7.91 (1H, m), 8.08 (1H, m).

EXAMPLE 2

A mixture of N-tert-butoxycarbonyl-D-phenylalanyl-S-methyl-D-cysteine ethyl ester (0.41 g), ethyl acetate (10 ml), and saturated solution of hydrogen chloride in ethyl acetate (10 ml) was stirred for 4 hours at room temperature. After removal of the solvent, the residue was dissolved in ethanol (10 ml) and saturated ammonia in ethanol (10 ml) was added to the solution. The resulting mixture was stirred for 17 hours at room temperature and the solvent was evaporated off. Recrystallization from acetic acid gave (3R,6S)-3-benzyl-6-methylthiomethylpiperazine-2,5-dione (0.08 g).

mp: 246°–247° C.

IR (Nujol): 1660 cm$^{-1}$.

NMR (DMSO-d$_6$) δ: 1.63 (1H, dd, J=14 Hz, 7 Hz), 1.85 (3H, s), 2.35 (1H, dd, J=14 Hz, 4 Hz), 2.92 (1H, dd, J=14 Hz, 5 Hz), 3.18 (1H, dd, J=14 Hz, 5 Hz), 3.82 (1H, m), 4.21 (1H, m), 7.22 (5H, s), 7.95 (1H, bs), 8.18 (1H, bs).

EXAMPLE 3

The following compounds were prepared in a similar manner to those of Example 1 and 2.

(1) (3R,6R)-3-Benzyl-6-(2-methylthioethyl)piperazine-2,5-dione mp: 253°–254° C.

IR (Nujol): 1665 cm$^{-1}$.

NMR (DMSO-d$_6$) δ: 1.15 (2H, m), 1.90 (3H, s), 1.95 (2H, m), 2.88 (1H, dd, J=13 Hz, 5 Hz), 3.20 (1H, dd, J=13 Hz, 3 Hz), 3.75 (1H, m), 4.23 (1H, m), 7.25 (5H, m), 8.10 (1H, s), 8.23 (1H, s).

(2) (3S,6R)-3-Benzylthiomethyl-6-(1-methylindol-3-ylmethyl)piperazine-2,5-dione.

mp. 229°–231° C.

IR (Nujol): 3180, 3050, 1660 cm$^{-1}$.

NMR (DMSO-d$_6$) δ: 1.73 (1H, dd, J=14 Hz, 7 Hz), 2.35 (1H, dd, J=14 Hz, 4 Hz), 3.16 (2H, m), 3.40 (2H, s), 3.65 (3H, s), 3.85 (1H, m), 4.13 (1H, m), 6.85–7.6 (10H, m), 7.92 (1H, d, J=1 Hz), 8.06 (1H, d, J=0.5 Hz).

(3) (3R,6S)-3-Benzyl-6-methylthiomethylpiperazine-2,5-dione mp: 246°–247° C.

IR (Nujol): 1660 cm$^{-1}$.

NMR (DMSO-d$_6$) δ: 1.63 (1H, dd, J=14 Hz, 7 Hz), 1.85 (3H, s), 2.35 (1H, dd, J=14 Hz, 4 Hz), 2.92 (1H, dd, J=14 Hz, 5 Hz), 3.18 (1H, dd, J=14 Hz, 5 Hz), 3.82 (1H, m), 4.21 (1H, m), 7.22 (5H, s), 7.95 (1H, bs), 8.13 (1H, bs).

(4) (3R,6R)-3-Indol-3-ylmethyl-6-(2-methylthioethyl)-piperazine-2,5-dione.

mp. 240°–241° C.

IR (Nujol): 3350, 3210, 3070, 1670 cm$^{-1}$.

NMR (DMSO-d$_6$) δ: 1.20 (2H, m), 1.70 (2H, m), 1.76 (3H, s), 3.18 (2H, m), 3.72 (1H, m), 4.19 (1H, m), 7.00 (3H, m), 7.20 (1H, m), 7.55 (1H, m), 7.90 (1H, m), 8.05 (1H, m), 10.68 (1H, bs).

(5) (3R,6S)-3-Indol-3-ylmethyl-6-methylthiomethylpiperazine-2,5-dione.

mp. 265°–268° C. (dec.).

IR (Nujol): 3430, 3190, 3050, 1680, 1660 cm$^{-1}$.

NMR (DMSO-d$_6$) δ: 1.58 (1H, dd, J=14 Hz, 7 Hz), 1.70 (3H, s), 2.30 (1H, dd, J=14 Hz, 4 Hz), 3.06 (1H, dd, J=17 Hz, 6 Hz), 3.35 (1H, dd, J=17 Hz, 6 Hz), 3.80 (1H, m), 4.16 (1H, m), 7.05 (3H, m), 7.35 (1H, dd, J=6 Hz, 2 Hz), 7.58 (1H, dd, J=6 Hz, 2 Hz), 7.90 (1H, bs), 8.08 (1H, bs), 10.85 (1H, bs).

(6) (3R,6RS)-3-Methylthiomethyl-6-phenethylpiperazine-2,5-dione mp. 221°–228° C.

IR (Nujol): 3310, 3180, 3030, 1685 cm$^{-1}$.

NMR (DMSO-d$_6$) δ: 2.10 (2H, m), 2.11 (3H, s), 2.70 (2H, m), 2.90 (2H, m), 4.00 (1H, m), 4.20 (1H, m), 7.25 (5H, m), 8.13 (1H, bs), 8.40 (1H, bs).

(7) (3S,6R)-3-Allylthiomethyl-6-(1-methylindol-3-ylmethyl)piperazine-2,5-dione.

mp. 210°–211° C.

IR (Nujol): 3180, 1660 cm$^{-1}$.

NMR (DMSO-d$_6$) δ: 1.78(1H, dd, J=14, 6 Hz), 2.35(1H, dd, J=14, 4 Hz), 2.85(2H, d, J=7 Hz), 3.19(2H, m), 3.70(3H, s), 3.80(1H, m), 4.13(1H, m), 4.92(1H, bs), 5.07(1H, m), 5.60(1H, m), 7.04(2H, m), 7.07(1H, s), 7.36(1H, d, J=7 Hz), 7.56(1H, d, J=7 Hz), 7.92(1H, bs), 8.06(1H, bs).

(8) (3R,6R)-3-(Indol-3-ylmethyl)-6-(2-methylthioethyl)-piperazine-2,5-dione mp. 254°-255° C.

IR (Nujol): 3430, 3200, 1680 cm$^{-1}$.

NMR (DMSO-d$_6$) δ: 1.80 (2H, m), 1.95 (3H, s), 3.40 (2H, m), 3.15 (2H, m), 3.35 (1H, m), 4.15 (1H, m), 7.10 (3H, m), 7.40 (1H, m), 7.63 (1H, m), 7.97 (1H, s), 8.11 (1H, d, J=0.5 Hz), 10.84 (1H, bs).

(9) (3R,6R)-3-n-Butylthiomethyl-6-(1-methylindol-3-ylmethyl)piperazine-2,5-dione mp. 200°-201° C.

IR (Nujol): 3180, 1675 cm$^{-1}$.

NMR (DMSO-d$_6$) δ: 0.84 (3H, m), 3.35 (4H, m), 2.4 (2H, m), 2.65 (1H, dd, J=14, 4 Hz), 2.87 (1H, dd, J=14, 4 Hz), 3.16 (2H, m), 3.47 (1H, m), 3.71 (3H, s), 4.20 (1H, m), 7.10 (3H, m), 7.40 (1H, m), 7.65 (1H, m), 7.85 (1H, bs), 8.18 (1H, bs).

(10) (3R,6S)-3-(1-Methylindol-3-ylmethyl)-6-(2-methylthioethyl)piperazine-2,5-dione mp. 234°-235° C.

IR (Nujol): 3190, 3050, 1675 cm$^{-1}$.

NMR (DMSO-d$_6$) δ: 1.80 (2H, m), 1.94 (3H, s), 2.35 (2H, m), 3.20 (3H, m), 4.70 (3H, s), 5.07 (1H, m), 6.95 (1H, m), 7.04 (1H, s), 7.15 (1H, m), 7.36 (1H, d, J=7.5 Hz), 7.59 (1H, d, J=7.5 Hz), 7.95 (1H, s), 8.05 (1H, bs).

(11) (3R,6R)-3-(Benzo[b]thien-3-ylmethyl)-6-(2-methylthioethyl)piperazine-2,5-dione IR (Nujol): 3180, 1660 cm$^{-1}$.

NMR (DMSO-d$_6$) δ: 1.25(2H, m), 1.78(2H, m), 1.80(3H, s), 3.20(1H, dd, J=14, 5 Hz), 3.43 (1H, dd, J=14, 4 Hz), 3.76(1H, m), 4.30(1H, m), 7.35(2H, m), 7.40(1H, s), 7.95(2H, m), 8.10 (1H, bs), 8.26(1H, bs).

(12) (3RS,6S)-3-Diphenylmethyl-6-methylthiomethyl-piperazine-2,5-dione mp. 250°-253° C.

IR (Nujol): 3180, 3050, 1670, 1655 cm$^{-1}$.

(13) (3S,6RS)-3-Methylthiomethyl-6-((RS)-1-phenylethyl)piperazine-2,5-dione mp. 258°-261° C.

IR (Nujol): 3180, 3050, 1655 cm$^{-1}$.

(14) (3R,6RS)-3-Methylthiomethyl-6-((RS)-1-phenylethyl)piperazine-2,5-dione mp. 264°-264.5° C.

IR (Nujol): 3190, 3050, 1660 cm$^{-1}$.

NMR (DMSO-d$_6$) δ: 0.82 (0.5H, d, J=9 Hz), 0.97 (0.5H, d, J=9 Hz), 1.34 (3H, d, J=7.5 Hz), 1.80 (1.5H, s), 1.96 (1.5H, s), 2.06 (0.5H, d, J=4 Hz), 2.21 (0.5H, d, J=4 Hz), 2.70 (1H, m), 3.50 (1H, m), 4.00 (1H, m), 7.20 (5H, m), 7.79 (0.5H, s), 7.89 (0.5H, d, J=3 Hz), 8.43 (1H, m).

(15) (3RS,6R)-3-Methylthiomethyl-6-phenylpiperazine-2,5-dione mp. 189°-190° C.

IR (Nujol): 3200, 1675 cm$^{-1}$.

NMR (DMSO-d$_6$) δ: 2.07 and 2.13 (3×0.25H, s, 3×0.75H, s, respectively), 2.85-3.20 (2H, m), 4.25 and 4.37 (2×0.25H, m, 2×0.75H, m, respectively), 5.00 and 5.02 (1×0.25H, s, 1×0.75H, s, respectively), 7.40 (5H, m), 8.16 and 8.25 (1×0.75H, bs, 1×0.25H, bs, respectively), 8.67 (1H, bs).

(16) (3R,6R)-3-Isobutyl-6-(1-methylindol-3-ylmethyl)-piperazine-2,5-dione.

mp. 234°-235° C.

IR (Nujol): 3200, 1665 cm$^{-1}$.

NMR (DMSO-d$_6$) δ: 0.15 (1H, m), 0.45 (3H, d, J=8 Hz), 0.51 (3H, d, J=8 Hz), 0.75 (1H, m), 1.20 (1H, m), 3.00 (1H, dd, J=14 Hz, 5 Hz), 3.26 (1H, m), 3.45 (1H, m), 3.70 (3H, s), 4.10 (1H, m), 6.96 (1H, m), 7.02 (1H, s), 7.10 (1H, m), 7.35 (1H, d, J=8 Hz), 7.60 (1H, d, J=8 Hz), 7.92 (1H, m), 8.03 (1H, m).

EXAMPLE 4

To a solution of (3R,6R)-3-(1-methylindol-3-ylmethyl)-6-(2-methylthioethyl)piperazine-2,5-dione (0.33 g) in dry dimethylformamide (20 ml) was added potassium tert-butoxide (0.27 g). After stirring at room temperature for 30 minutes, methyl iodide (0.5 ml) was added to the mixture. The reaction mixture was stirred for 5 minutes, diluted with water (200 ml), acidified to pH 3 with 10% hydrochloric acid, and extracted with ethyl acetate (50 ml×2). Combined organic extract was washed with water, dried over magnesium sulfate, and evaporated in vacuo. The residue (0.25 g) was chromatographed on silica gel (11 g) using chloroform as eluent to give (3R,6R)-1,4-dimethyl-3-(1-methylindol-3-ylmethyl)-6-(2-methylthioethyl)piperazine-2,5-dione (0.08 g) as an oil.

IR (CHCl$_3$): 2990, 2920, 1650 cm$^{-1}$.

NMR (CDCl$_3$) δ: 0.40 (1H, m), 0.75 (1H, m), 1.83 (3H, s), 2.06 (2H, dd, J=7 Hz, 7 Hz), 2.70 (3H, s), 3.00 (3H, s), 3.23 (1H, dd, J=14 Hz, 4 Hz), 3.54 (1H, dd, J=6 Hz, 4 Hz), 3.70 (1H, dd, J=14 Hz, 4 Hz), 3.73 (3H, s), 4.19 (1H, t, J=4 Hz), 6.80 (1H, s), 7.20 (3H, m), 7.55 (1H, m).

EXAMPLE 5

(1) Sodium borohydride (2.1 g) was added to a solution of 1-acetylnaphthalene (18.86 g) in ethanol (200 ml) at room temperature and the mixture was stirred at the same temperature for 2 hours. The mixture was diluted with water (50 ml), acidified to pH 3 with 1N hydrochloric acid and concentrated to about 70 ml. The concentrate was extracted with ethyl acetate (100 ml×2). The extract was dried over magnesium sulfate and evaporated to give 1-(1-hydroxyethyl)naphthalene as an oil which was used in a next reaction without further purification. Hydrogen bromide was bubbled into a solution of 1-(1-hydroxyethyl)naphthalene (18.96 g) in ether (180 ml) for 2 hours under ice-bath cooling. The reaction mixture was washed with water (50 ml×2), 2.5% sodium bicarbonate (50 ml×2) and water (50 ml×2), dried over magnesium sulfate and evaporated to give 1-(1-bromoethyl)naphthalene (22.63 g).

NMR (CDCl$_3$) δ: 2.23 (3H, d, J=6 Hz), 5.97 (1H, q, J=6 Hz), 7.2-8.3 (7H, m).

(2) 2-Acetylaminopropanedioic acid diethyl ester (20.8 g) was added to a solution of sodium ethoxide in ethanol (prepared from sodium (2.2 g) and ethanol (100 ml). After the mixture was stirred for 10 minutes at ambient temperature, 1-(1-bromoethyl)naphthalene was added. The reaction mixture was stirred for 18 hours at room temperature. The precipitated solid was collected by filtration and dissolved in chloroform. The chloroform solution was dried over magnesium sulfate and evaporated to give 2-acetylamino-2-[1-(1-naphthyl)ethyl]propanedioic acid diethyl ester (21.59 g).

NMR (CDCl$_3$) δ: 0.87 (3H, t, J=9 Hz), 1.27 (3H, t, J=9 Hz), 1.58 (3H, d, J=9 Hz), 1.97 (3H, s), 3.1-4.0

(2H, m), 4.27 (2H, q, J=2 Hz), 5.00 (1H, q, J=9 Hz), 6.57 (1H, s), 7.2-8.3 (7H, m).

(3) A solution of 2-acetylamino-2-[1-(1-naphthyl)ethyl]propanedioic acid diethyl ester (21.59 g) in a mixture of concentrated hydrochloric acid (100 ml) and acetic acid (70 ml) was refluxed for 13 hours. The mixture was concentrated under reduced pressure and the residue was dissolved in water (100 ml). The solution was neutralized to pH 5 with 30% sodium hydroxide. The precipitated crystalline solid was collected by filtration to give 2-amino-3-(1-naphthyl)butyric acid (9.76 g).

Mass: 229 (M+).

(4) A solution of di-tert-butyl dicarbonate (13.95 g) in dioxane (128 ml) was added to a solution of 2-amino-3-(1-naphthyl)butyric acid (9.76 g) in 1N sodium hydroxide (128 ml) and the mixture was stirred for 1 hour at 50° C. The mixture was acidified to pH 3 with concentrated hydrochloric acid and concentrated to about 100 ml. The concentrate was extracted with ethyl acetate (100 ml×2). The extract was dried over magnesium sulfate and evaporated. The residue was chromatographed on a silica gel (500 ml) using chloroform-methanol (50:1) as eluent to give erythro-2-tert-butoxycarbonylamino-3-(1-naphthyl)butyric acid (6.58 g).

NMR (CDCl$_3$) δ: 1.3-1.6 (12H, br s), 3.9-5.0 (3H, m), 7.3-8.3 (8H, m).

Mass: 329 (M+).

(5) To a suspension of erythro-2-tert-butoxycarbonylamino-3-(1-naphthyl)butyric acid (2.50 g) and hydrochloric acid salt of D-methionine ethyl ester (1.62 g) in dry methylene chloride (60 ml) which was cooled on an ice bath and stirred was added triethylamine (0.77 g). The mixture was stirred at ambient temperature for 30 minutes, and to the mixture was added N,N'-dicyclohexylcarbodiimide (1.57 g). The resulting mixture was stirred overnight. After removal of the solvent, crude residue was taken up with a mixture of ethyl acetate and water and filtered and the organic layer was washed with 10% hydrochloric acid and saturated aqueous solution of sodium bicarbonate, dried over magnesium sulfate and evaporated to give a solid (4.29 g). To a solution of the solid in ethyl acetate (40 ml) was added a saturated solution of hydrogen chloride in ethyl acetate (40 ml) and the mixture was set aside at room temperature overnight. After removal of the solvent, crude residue was chromatographed on silica gel (200 g, a mixture of chloroform and methanol as an eluent).

The fractions containing the object compound were collected and concentrated under reduced pressure to give hydrochloric acid salt of N-[(2R,3R)-2-amino-3-(1-naphthyl)butyryl]-D-methionine ethyl ester (1.60 g) as an oil.

IR (Neat): 3200, 1710, 1670 cm$^{-1}$.

(6) To a solution of hydrochloric acid salt of N-[(2R,3R)-2-amino-3-(1-naphthyl)butyryl]-D-methionine ethyl ester (1.60 g) in ethanol (30 ml) was added a saturated solution of ammonia in ethanol (30 ml) and the mixture was set aside overnight at ambient temperature, and precipitated mass was collected, washed with ethanol, and dried to give (3R,6R)-3-(2-methylthioethyl)-6-[(R)-1-(1-naphthyl)ethyl]piperazine-2,5-dione (0.68 g).

mp: 265°-268° C.

IR (Nujol): 3200, 1675, 1660 cm$^{-1}$.

NMR (DMSO-d$_6$) δ: 0.38 (1H, m), 1.02 (1H, m), 1.49 (3H, d, J=8.1 Hz), 1.69 (2H, t, J=8.1 Hz), 1.73 (3H, s), 3.60 (1H, m), 4.19 (1H, s), 4.41 (1H, m), 7.51 (4H, m), 7.95 (3H, m), 8.30 (1H, m), 8.54 (1H, m).

EXAMPLE 6

The following compounds were prepared in a similar manner to that of Example 5 (6).

(1) (3R,6R)-3-(2-Ethoxycarbonylethyl)-6-(1-methylindol-3-ylmethyl)piperazine-2,5-dione
mp: 197°-202° C.
IR (Nujol): 3180, 3050, 1730, 1670 cm$^{-1}$.
NMR (DMSO-d$_6$) δ: 1.14 (3H, t, J=6 Hz), 1.25 (4H, m), 2.97 (1H, dd, J=14, 5 Hz), 3.26 (1H, dd, J=14, 4 Hz), 3.65 (1H, m), 3.96 (2H, q, J=6 Hz), 4.15 (1H, m), 7.03 (1H, s), 7.05 (2H, m), 7.32 (1H, dd, J=7, 1 Hz), 7.65 (1H, dd, J=7, 1 Hz), 7.96 (1H, br s), 8.20 (1H, br s).

(2) (3R,6R)-3-[(R)-sec-Butyl]-6-(1-methylindol-3-ylmethyl)piperazine-2,5-dione
IR (Nujol): 3180, 3040, 1660 cm$^{-1}$.
NMR (DMSO-d$_6$) δ: 0.14 (3H, d, J=7 Hz), 0.65 (3H, m), 1.00 (2H, m), 1.40 (1H, m), 3.05 (1H, dd, J=15, 5 Hz), 3.25 (1H, dd, J=15, 4 Hz), 3.63 (1H, m), 4.16 (1H, m), 7.04 (1H, s), 7.05 (2H, m), 7.35 (1H, dd, J=7, 1 Hz), 7.65 (1H, dd, J=7, 1 Hz), 7.75 (1H, s), 7.97 (1H, s).

(3) (3R,6R)-3-(1-Methylindol-3-ylmethyl)-6-(2-phenylthioethyl)piperazine-2,5-dione
mp: 176°-182° C.
IR (Nujol): 3180, 1675, 1660 cm$^{-1}$.
NMR (DMSO-d$_6$) δ: 1.20 (2H, m), 1.9-2.2 (2H, m), 2.9-3.5 (6H, m), 4.15 (1H, m), 6.9-7.4 (9H, m), 7.60 (1H, m), 8.00 (1H, d, J=1 Hz), 8.17 (1H, br s).

(4) (3R,6R)-3-Diphenylmethyl-6-(2-methylthioethyl)piperazine-2,5-dione
mp: 279°-281° C.
IR (Nujol): 3200, 3050, 1665 cm$^{-1}$.
NMR (DMSO-d$_6$) δ: 1.05 (1H, m), 1.40 (1H, m), 1.93 (3H, s), 2.16 (2H, t, J=7.5 Hz), 3.80 (1H, m), 4.60 (1H, d, J=4.5 Hz), 4.80 (1H, m), 7.30 (10H, s), 7.96 (1H, d, J=1 Hz), 8.16 (1H, d, J=1 Hz).

(5) (3R,6R)-3-[(R)-α-Methoxybenzyl]-6-(2-methylthioethyl)piperazine-2,5-dione
mp: 253°-258° C.
IR (Nujol): 3190, 3050, 1670, 1660 cm$^{-1}$.

(6) (3R,6R)-3,6-bis(1-Methylindol-3-ylmethyl)piperazine-2,5-dione
mp: 263°-265° C.
NMR (DMSO-d$_6$) δ: 2.21 (2H, dd, J=14, 6 Hz), 2.75 (2H, dd, J=14, 4.5 Hz), 3.67 (6H, s), 3.90 (2H, m), 6.59 (2H, s), 6.9-7.5 (8H, m), 7.74 (2H, d, J=0.5 Hz).

(7) (3R,6S)-3-(1-Methylindol-3-ylmethyl)-6-phenylthiomethylpiperazine-2,5-dione
mp: 216°-219° C.
IR (Nujol): 3190, 3050, 1670 cm$^{-1}$.
NMR (DMSO-d$_6$) δ: 2.06 (1H, dd, J=13, 7 Hz), 2.73 (1H, dd, J=13, 4 Hz), 3.06 (1H, dd, J=14, 4 Hz), 3.30 (1H, dd, J=14, 5 Hz), 3.65 (3H, s), 4.83 (1H, m), 4.17 (1H, m), 6.9-7.4 (9H, m), 7.61 (1H, d, J=8 Hz), 8.06 (1H, d, J=1 Hz), 8.20 (1H, d, J=0.5 Hz).

(8) (3R,6R)-3-(1-Methylindol-3-ylmethyl)-6-(3-methylthiopropyl)piperazine-2,5-dione
mp: 209°-210° C.
IR (Nujol): 3180, 3040, 1675, 1660 cm$^{-1}$.
NMR (DMSO-d$_6$) δ: 0.55-1.2 (4H, m), 1.83 (3H, s), 1.98 (2H, t, J=7 Hz), 2.97 (1H, dd, J=14, 5 Hz), 3.26 (1H, dd, J=14, 4 Hz), 3.55 (1H, m), 3.73 (3H, s), 4.14 (1H, m), 6.9-7.2 (2H, m), 7.03 (1H, s), 7.38 (1H, d, J=8 Hz), 7.62 (1H, d, J=8 Hz), 7.96 (1H, br s), 8.06 (1H, d, J=0.5 Hz).

(9) (3R,6RS)-3-(2-Methylthioethyl)-6-(2-naphthylmethyl)piperazine-2,5-dione
mp: 179° C.

IR (Nujol): 3170, 3040, 1670 cm$^{-1}$.

(10) (3R,6R)-3-(4-Methoxybenzyl)-6-(2-methylthioethyl)piperazine-2,5-dione
mp: 266°–267° C.
IR (Nujol): 3180, 1660 cm$^{-1}$.
NMR (DMSO-d$_6$) δ: 1.25 (2H, m), 1.88 (3H, s), 1.93 (2H, t, J=8 Hz), 2.78 (1H, dd, J=14, 5 Hz), 3.13 (1H, dd, J=14, 4 Hz), 3.71 (3H, s), 3.75 (1H, m), 4.17 (1H, m), 6.85 (2H, d, J=9 Hz), 7.11 (2H, d, J=9 Hz), 8.08 (1H, s), 8.19 (1H, s).

(11) (3R,6RS)-3-(2-Methylthioethyl)-6-(2-pyridylmethyl)piperazine-2,5-dione
mp: 163°–165° C.
IR (Nujol): 3180, 3040, 1675 cm$^{-1}$.

(12) (3R,6R)-3-(2-Methylthioethyl)-6-(1-naphthylmethyl)piperazine-2,5-dione
mp: 236°–240° C.
IR (Nujol): 3180, 3050, 1670 cm$^{-1}$.
NMR (DMSO-d$_6$) δ: 1.20 (2H, m), 1.86 (3H, s), 1.90 (2H, m), 3.49 (1H, m), 3.55 (1H, m), 3.71 (1H, m), 4.30 (1H, m), 7.50 (4H, m), 7.90 (2H, m), 8.20 (3H, m).

(13) (3R,6R)-3-(1-Methylindol-3-ylmethyl)-6-methylthiomethylpiperazine-2,5-dione
mp: 244°–247° C.

(14) (3R,6R)-3-Butyl-6-(1-methylindol-3-ylmethyl)piperazine-2,5-dione
mp: 237°–239° C.
IR (Nujol): 3180, 3040, 1665 cm$^{-1}$.
NMR (DMSO-d$_6$) δ: 0.4–1.2 (9H, m), 3.00 (1H, dd, J=15, 5 Hz), 3.25 (1H, dd, J=15, 4 Hz), 3.53 (1H, m), 3.70 (3H, s), 4.13 (1H, m), 7.01 (1H, s), 7.03 (2H, m), 7.33 (1H, dd, J=8, 1 Hz), 7.62 (1H, dd, J=8, 1 Hz), 7.89 (1H, br s), 8.01 (1H, br s).

(15) (3R,6R)-3-(1-Methylindol-3-ylmethyl)-6-Octylpiperazine-2,5-dione
mp: 211°–213° C.
IR (Nujol): 3170, 3040, 1660 cm$^{-1}$.
NMR (DMOS-d$_6$) δ: 0.5–1.4 (17H, m), 3.03 (1H, dd, J=15, 5 Hz), 3.30 (1H, dd, J=15, 4 Hz), 3.55 (1H, m), 3.73 (3H, s), 4.15 (1H, m), 7.03 (1H, s), 7.05 (2H, m), 7.35 (1H, dd, J=7, 1 Hz), 7.63 (1H, dd, J=7, 1 Hz), 7.92 (1H, br s), 8.03 (1H, br s).

(16) (3R,6R)-3-Dodecyl-6-(1-methylindol-3-ylmethyl)piperazine-2,5-dione
mp: 207°–209° C.
IR (Nujol): 3160, 3030, 1660 cm$^{-1}$.
NMR (DMSO-d$_6$) δ: 0.4–1.4 (25H, m), 2.95 (1H, dd, J=14, 5 Hz), 3.23 (1H, dd, J=14, 4 Hz), 3.47 (1H, m), 3.68 (3H, s), 4.09 (1H, m), 7.00 (1H, s), 7.00 (2H, m), 7.30 (1H, dd, J=7, 1 Hz), 7.58 (1H, dd, J=7, 1 Hz), 7.87 (1H, br s), 8.00 (1H, br s).

(17) (3R,6R)-3-[(S)-1-(2-Naphthyl)ethyl]-6-(2-methylthioethyl)piperazine-2,5-dione
mp: 287°–288° C.
IR (Nujol): 3190, 3140, 1660 cm$^{-1}$.
NMR (DMSO-d$_6$) δ: 0.60 (1H, m), 1.00 (1H, m), 1.46 (3H, d, J=8 Hz), 1.48 (3H, s), 1.70 (2H, t, J=8 Hz), 3.65 (2H, m), 4.10 (1H, m), 7.3–7.9 (7H, m), 8.01 (1H, m), 8.40 (1H, m).

(18) (3R,6R)-3-(2-Methylthioethyl)-6-[(RS)-1-phenylethyl]piperazine-2,5-dione
mp: 273°–276° C.
IR (Nujol): 3180, 1660 cm$^{-1}$.
NMR (DMSO-d$_6$) δ: 0.60 (1H, m), 1.10 (1H, m), 1.33 (3H, d, J=7 Hz), 1.83 (3H, s), 1.93 (2H, t, J=7.5 Hz), 3.5 (2H, m), 3.96 (1H, m), 7.20 (5H, m), 8.00 (1H, br s), 8.30 (1H, br s).

(19) (3R,6R)-3-(3-Benzyloxycarbonylaminopropyl)-6-(1-methylindol-3-ylmethyl)piperazine-2,5-dione
mp: 170°–172° C.
IR (Nujol): 3310, 3190, 1715, 1665 cm$^{-1}$.
NMR (DMSO-d$_6$) δ: 0.6–1.2 (4H, m), 2.60 (2H, m), 3.02 (1H, dd, J=15, 5 Hz), 3.26 (1H, dd, J=15, 4 Hz), 3.57 (1H, m), 3.70 (3H, s), 4.13 (1H, m), 5.00 (2H, s), 7.00 (4H, m), 7.30 (1H, m), 7.35 (5H, s), 7.60 (1H, d, J=7, 1 Hz), 7.92 (1H, d, J=1 Hz), 8.01 (1H, d, J=1 Hz).

(20) (3R,6R)-3-(9-Anthrylmethyl)-6-(2-methylthioethyl)piperazine-2,5-dione
mp: 299°–304° C.
IR (Nujol): 3180, 3050, 1660 cm$^{-1}$.
NMR (DMSO-d$_6$) δ: 1.56 (1H, m), 1.74 (1H, m), 2.02 (3H, s), 2.37 (2H, t, J=7.5 Hz), 3.78 (1H, m), 4.02 (1H, dd, J=13.5, 7.5 Hz), 4.12 (1H, dd, J=13.5, 5 Hz), 7.52 (4H, m), 7.96 (1H, d, J=2.5 Hz), 8.09 (2H, dd, J=8, 2 Hz), 8.33 (2H, d, J=8 Hz), 8.35 (1H, s), 8.55 (1H, s).

(21) (3R,6R)-3-(1-Methylindol-3-ylmethyl)-6-pentylpiperazine-2,5-dione
mp: 228° C.
IR (Nujol): 3190, 3050, 1680, 1670 cm$^{-1}$.
NMR (DMSO-d$_6$) δ: 0.5–1.2 (11H, m), 2.98 (1H, dd, J=15, 5 Hz), 3.25 (1H, dd, J=15, 4 Hz), 3.50 (1H, m), 3.70 (3H, s), 4.10 (1H, m), 6.8–7.2 (2H, m), 7.00 (1H, s), 7.31 (1H, dd, J=8, 1 Hz), 7.60 (1H, dd, J=8, 1 Hz), 7.89 (1H, br s), 7.99 (1H, br s).

(22) (3R,6R)-3-[(S)-1-(1-Naphthyl)ethyl]-6-(2-methylthioethyl)piperazine-2,5-dione
mp: 290°–293° C.
IR (Nujol): 3180, 3040, 1660 cm$^{-1}$.

(23) (3R,6S)-3-(1-Methylindol-3-ylmethyl)-6-(2-phenylthioethyl)piperazine-2,5-dione
mp: 204°–208° C.
IR (Nujol): 3180, 3050, 1675 cm$^{-1}$.

(24) (3R,6R)-3-(1-Methylindol-3-ylmethyl)-6-phenylthiomethylpiperazine-2,5-dione
mp: 213°–214° C.
IR (Nujol): 3180, 3050, 1660 cm$^{-1}$.
NMR (DMSO-d$_6$) δ: 3.02 (1H, dd, J=14, 4.5 Hz), 3.23 (3H, m), 3.50 (1H, m), 3.70 (3H, s), 4.20 (1H, m), 6.9–7.4 (3H, m), 7.05 (1H, s), 7.29 (5H, s), 7.62 (1H, dd, J=8, 1 Hz), 7.95 (1H, s), 8.23 (1H, s).

(25) (3R,6S)-3-(1-Methylindol-3-ylmethyl)-6-(3-methylthiopropyl)piperazine-2,5-dione
mp: 205°–206° C.
IR (Nujol): 3230, 1670, 1635 cm$^{-1}$.
NMR (DMSO-d$_6$) δ: 1.59 (4H, m), 2.00 (3H, s), 2.38 (2H, t, J=7 Hz), 2.95–3.5 (3H, m), 3.75 (3H, s), 4.13 (1H, m), 6.9–7.3 (2H, m), 7.10 (1H, s), 7.42 (1H, d, J=8 Hz), 7.65 (1H, d, J=8 Hz), 7.98 (1H, s), 8.05 (1H, d, J=1 Hz).

(26) (3R,6S)-3-(1-Methylindol-3-ylmethyl)-6-octylpiperazine-2,5-dione
mp: 201°–202° C.
IR (Nujol): 3170, 3040, 1665 cm$^{-1}$.
NMR (DMSO-d$_6$) δ: 0.86 (3H, m), 1.20 (12H, m), 1.53 (2H, m), 3.15 (3H, m), 3.72 (3H, s), 4.10 (1H, m), 7.05 (2H, m), 7.06 (1H, s), 7.36 (1H, dd, J=7, 1 Hz), 7.60 (1H, dd, J=7, 1 Hz), 7.88 (1H, br s), 7.98 (1H, br s).

(27) (3S,6R)-3-Dodecyl-6-(1-methylindol-3-ylmethyl)piperazine-2,5-dione
mp: 187°–188° C.
IR (Nujol): 3160, 1670, 1660 cm$^{-1}$.
NMR (DMSO-d$_6$) δ: 0.8–1.6 (25H, m), 3.1 (3H, m), 3.70 (3H, s), 4.05 (1H, m), 6.9–8.0 (7H, m).

(28) (3S,6R)-3-(3-Benzyloxycarbonylaminopropyl)-6-(1-methylindol-3-ylmethyl)piperazine-2,5-dione
mp: 128°–130° C.

IR (Nujol): 3330, 3190, 1670 cm$^{-1}$.

NMR (DMSO-d$_6$) δ: 1.43 (4H, m), 2.8–3.3 (5H, m), 3.70 (3H, s), 4.05 (1H, m), 4.97 (2H, s), 7.03 (4H, m), 7.30 (5H, s), 7.30 (1H, m), 7.58 (1H, dd, J=8, 1 Hz), 7.87 (1H, s), 8.00 (1H, d, J=1 Hz).

(29) (3R,6RS)-3-(1-Methylindol-3-ylmethyl)-6-pentylpiperazine-2,5-dione
mp: 204°–212° C.

IR (Nujol): 3200, 1680 cm$^{-1}$.

NMR (DMSO-d$_6$) δ: 0.80 (3H, m), 1.15 (6H, m), 1.46 (2H, m), 2.9–3.3 (3H, m), 3.70 (3H, s), 4.07 (1H, m), 6.85–7.2 (2H, m), 7.02 (1H, s), 7.33 (1H, dd, J=7, 2 Hz), 7.57 (1H, dd, J=7, 2 Hz), 7.86 (1H, s), 7.92 (1H, br s).

(30) (3R,6R)-3-(1-Methyl-2-phenylindol-3-ylmethyl)-6-(2-methylthioethyl)piperazine-2,5-dione
mp: 295°–298° C.

IR (Nujol): 3200, 1670, 1660 cm$^{-1}$.

NMR (DMSO-d$_6$) δ: 1.0–1.6 (2H, m), 1.90 (3H, s), 2.03–2.90 (2H, m), 2.8–3.1 (2H, m), 3.50 (3H, s), 3.5–4.0 (2H, m), 7.0–8.1 (11H, m).

(31) (3R,6R)-3-(1-Methylindol-3-ylmethyl)-6-propylpiperazine-2,5-dione
mp: 241°–243° C.

IR (Nujol): 3200, 1665, 1660 cm$^{-1}$.

NMR (DMSO-d$_6$) δ: 0.3–1.2 (7H, m), 3.0–3.3 (2H, m), 3.4–3.6 (1H, m), 3.70 (3H, s), 4.0–4.2 (1H, m), 6.9–8.1 (7H, m).

(32) (3R,6R)-3-Butyl-6-[(R)-1-(1-naphthyl)ethyl]piperazine-2,5-dione
mp: 279°–281° C.

IR (Nujol): 3200, 1670, 1660 cm$^{-1}$.

NMR (DMSO-d$_6$) δ: −0.21–0.0 (1H, m), 0.34–0.82 (8H, m), 1.47 (3H, d, J=7.9 Hz), 3.32 (1H, m), 4.11 (1H, s), 4.34 (1H, m), 7.39 (4H, m), 7.76 (3H, m), 8.16 (1H, m), 8.42 (1H, m).

(33) (3R,6R)-3-(1-Methylindol-3-ylmethyl)-6-benzylpiperazine-2,5-dione
mp: 283°–284° C.

IR (Nujol): 3110, 1660 cm$^{-1}$.

NMR (DMSO-d$_6$) δ: 2.00 (1H, dd, J=13.5, 6 Hz), 2.37 (1H, dd, J=14.5, 6 Hz), 2.46 (1H, dd, J=13.5, 6 Hz), 2.77 (1H, dd, J=14.5, 4 Hz), 3.45 (1H, m), 3.90 (1H, m), 6.78 (2H, m), 6.97 (1H, s), 7.0–7.25 (5H, m), 7.38 (1H, d, J=8 Hz), 7.48 (1H, d, J=8 Hz), 7.80 (1H, br s), 7.93 (1H, br s).

(34) (3R,6R)-3-(1-Methylindol-3-ylmethyl)-6-phenethylpiperazine-2,5-dione
mp: 240°–242° C.

IR (Nujol): 3170, 1660 cm$^{-1}$.

NMR (DMSO-d$_6$) δ: 0.97 (1H, m), 1.25 (1H, m), 1.79 (2H, m), 3.00 (1H, dd, J=15, 4.5 Hz), 3.30 (1H, dd, J=15, 4 Hz), 3.53 (3H, s), 3.62 (1H, m), 4.27 (1H, br s), 6.77 (2H, d, J=7.5 Hz), 7.0–7.3 (7H, m), 7.65 (1H, d, J=7.5 Hz), 8.03 (1H, s), 8.17 (1H, s).

(35) (3R,6S)-3-(1-Methylindol-3-ylmethyl)-6-phenethylpiperazine-2,5-dione
mp: 218°–220° C.

IR (Nujol): 3170, 1660 cm$^{-1}$.

NMR (DMSO-d$_6$) δ: 1.81 (2H, m), 2.50 (2H, m), 3.0–3.3 (2H, m), 3.71 (3H, s), 4.10 (1H, m), 7.0–7.3 (8H, m), 7.36 (1H, d, J=8 Hz), 7.60 (1H, d, J=8 Hz), 8.08 (1H, s), 8.11 (1H, s).

(36) (3R,6RS)-3-(2-Methylthioethyl)-6-phenethylpiperazine-2,5-dione
mp: 231°–233° C.

NMR (DMSO-d$_6$) δ: 1.98 (4H, m), 2.05 (3H, m), 2.55 (4H, m), 3.90 (1H, m), 4.00 (1H, m), 7.25 (5H, m), 8.28 (1H, s), 8.35 (1H, s).

(37) (3R,6R)-3-Hydroxymethyl-6-(1-methylindol-3-ylmethyl)piperazine-2,5-dione
mp: 233°–235° C.

IR (Nujol): 3150, 1670 cm$^{-1}$.

NMR (DMSO-d$_6$) δ: 3.2 (4H, m), 3.7 (1H, m), 3.73 (3H, s), 4.02 (1H, m), 4.92 (1H, t, J=5 Hz), 7.1 (3H, m), 7.40 (1H, dd, J=7, 2 Hz), 7.57 (1H, dd, J=7, 2 Hz), 7.85 (2H, m), 7.38 (1H, d, J=8 Hz), 7.58 (1H, d, J=8 Hz) 8.16 (1H, m), 8.22 (1H, m).

(38) (3R,6R)-3-(2-Benzyloxycarbonylethyl)-6-(1-methylindol-3-ylmethyl)piperazine-2,5-dione
mp: 207°–208° C.

IR (Nujol): 3160, 1720, 1655 cm$^{-1}$.

NMR (DMSO-d$_6$) δ: 1.15 (2H, m), 1.25 (2H, m), 2.97 (1H, dd, J=14, 4.5 Hz), 3.28 (1H, dd, J=14, 3.5 Hz), 3.60 (3H, s), 3.68 (1H, m), 4.15 (1H, m), 4.99 (2H, s), 6.92–7.48 (9H, m), 7.61 (1H, d, J=8 Hz), 7.97 (1H, s), 8.22 (1H, s).

(39) (3R,6R)-3-Benzyloxymethyl-6-(1-methylindol-3-ylmethyl)piperazine-2,5-dione
mp: 210°–211° C.

IR (Nujol): 3170, 1660 cm$^{-1}$.

NMR (DMSO-d$_6$) δ: 2.71 (1H, dd, J=10, 5 Hz), 3.05 (1H, dd, J=14.5, 4.5 Hz), 3.18 (1H, dd, J=14.5, 5 Hz), 3.26 (1H, dd, J=10, 3 Hz), 3.68 (3H, s), 3.81 (1H, m), 4.06 (1H, m), 4.15 (1H, d, J=13 Hz), 4.23 (1H, d, J=13 Hz), 6.94–7.50 (10H, m), 8.05 (2H, s).

(40) (3R,6R)-3-(1-Methylindol-3-ylmethyl)-6-(2-pyridylmethyl)piperazine-2,5-dione
mp: 188°–192° C.

(41) (3R,6S)-3-(1-Methylindol-3-ylmethyl)-6-(2-pyridylmethyl)piperazine-2,5-dione
mp: 197°–201° C.

(42) (3R,6R)-3-[(S)-1-(1-Methylindol-3-yl)ethyl]-6-(2-methylthioethyl)piperazine-2,5-dione
mp: 264°–267° C.

(43) (3R,6R)-3-[(R)-1-(1-Methylindol-3-yl)ethyl]-6-(2-methylthioethyl)piperazine-2,5-dione
mp: 279°–280° C.

(44) (3R,6R)-3-Butyl-6-[(R)-1-(1-methylindol-3-yl)ethyl]piperazine-2,5-dione
mp: 285°–288° C.

(45) (3R,6S)-3-(1-Methylindol-3-ylmethyl)-6-methylthiomethylpiperazine-2,5-dione
mp: >260° C.

EXAMPLE 7

(1) To a mixture of 1-methylindole (4.26 g) and methyl (2R,3R)-N-benzyloxycarbonyl-3-methyl-2-aziridinecarboxylate (2.70 g) in dry methylene chloride (50 ml) was added boron trifluoride etherate (1.33 ml) under ice-bath cooling. The mixture was stirred for five minutes at ambient temperature and the solvent was evaporated off. The residue was chromatographed on silica gel (chloroform and a 1:1 mixture of hexane and ether as eluent) to give (αR,βR)-N-benzyloxycarbonyl-1,β-dimethyltryptophane methyl ester (1.62 g) as an oil.

IR (Neat): 1715, 1670 cm$^{-1}$.

(2) A solution of (αR,βR)-N-benzyloxycarbonyl-1,β,dimethyltryptophane methyl ester (1.62 g) in methanol (50 ml) containing 10% paradium charcoal (300 mg) was hydrogenated at the ambient temperature and atmospheric pressure. After removal of the catalyst and evaporation of the solvent, the residual oil (1.13 g) was dissolved in methanol (5 ml) and to the solution, a solution of p-toluenesulfonic acid mono hydrate (0.81 g) in a mixture of water (2 ml) and methanol (2 ml) was added. The solution was evaporated to dryness to give p-toluenesulfonic acid salt of (αR,βR)-1,β-dimethyltryptophane methyl ester (1.77 g).

IR (Neat): 3200, 1715 cm⁻¹.

(3) The following compound was prepared in a similar manner to that of Example 5 (1).

N-[N-tert-Butoxycarbonyl-D-leucyl]-(αR,βR)-1,β-dimethyltryptophane methyl ester

IR (Nujol): 1715, 1670 cm⁻¹.

(4) The following compound was prepared in a similar manner to that of Example 5 (2).

(3R,6R)-3-Isobutyl-6-[(R)-1-(1-methylindol-3-yl)ethyl]-piperazine-2,5-dione

IR (Nujol): 3150, 1680 cm⁻¹.

EXAMPLE 8

A solution of (3R,6R)-3-(3-benzyloxycarbonylaminopropyl)-6-(1-methylindol-3-ylmethyl)piperazine-2,5-dione (1.2 g) in ethanol (240 ml) containing 10% paradium on charcoal (0.6 g) was hydrogenated at ambient temperature and atmospheric pressure. After catalyst was filtered off and solvent was evaporated, crude solid was taken up with ethanol, and dried in vacuo to give (3R,6R)-3-(3-aminopropyl)-6-(1-methylindol-3-ylmethyl)piperazine-2,5-dione.

mp: 148° C.

EXAMPLE 9

The following compound was prepared in a similar manner to that of Example 8.

(3S,6R)-3-(3-Aminopropyl)-6-(1-methylindol-3-ylmethyl)piperazine-2,5-dione mp: 175°–177° C.

EXAMPLE 10

To a solution of (3R,6R)-3-(3-aminopropyl)-6-(1-methylindol-3-ylmethyl)piperazine-2,5-dione (100 mg) in dry N,N-dimethylformamide (3 ml) was added benzoyl chloride (60 mg). The mixture was stirred at ambient temperature for 2 hours, diluted with water (15 ml) and allowed to stand overnight. The precipitated mass was collected, washed with water, and dried in vacuo to give (3R,6R)-3-(3-benzamidopropyl)-6-(1-methylindol-3-ylmethyl)piperazine-2,5-dione (45 mg).

mp: 238°–239° C.

IR (Nujol): 3320, 1675, 1630 cm⁻¹.

NMR (DMSO-$d_6$) δ: 0.85 (3H, m), 1.08 (1H, m), 2.87 (2H, m), 3.00 (1H, dd, J=14, 4.5 Hz), 3.23 (1H, dd, J=14, 4 Hz), 3.59 (1H, m), 3.70 (3H, s), 4.11 (1H, m), 7.05 (3H, m), 7.29 (1H, d, J=8 Hz), 7.45 (3H, m), 7.58 (1H, d, J=8 Hz), 7.80 (2H, m), 7.99 (1H, s), 8.09 (1H, s), 8.24 (1H, t, J=5.5 Hz).

EXAMPLE 11

A mixture of (3R,6R)-3-hydroxymethyl-6-(1-methylindol-3-ylmethyl)-piperazine-2,5-dione (0.10 g), dry pyridine (1.0 ml) and acetic anhydride (0.08 g) was heated at 100° C. for 1 hour. After the mixture was cooled to ambient temperature, the pricipitated mass was collected, washed with pyridine and then ethanol, and dried to give (3R,6R)-3-acetoxymethyl-6-(1-methylindol-3-ylmethyl)piperazine-2,5-dione (61.8 mg).

mp: 250°–252° C.

IR (Nujol): 3180, 1735, 1670, 1660 cm⁻¹.

NMR (DMSO-$d_6$) δ: 1.85 (3H, s), 3.10 (1H, dd, J=15, 4.5 Hz), 3.18 (1H, dd, J=15, 4.5 Hz), 3.23 (1H, dd, J=10.5, 5.5 Hz), 3.73 (3H, s), 3.81 (1H, dd, J=10.5, 3.5 Hz), 3.98 (1H, m), 4.11 (1H, m), 7.00 (1H, dd, J=8, 7 Hz), 7.09 (1H, s), 7.12 (1H, t, J=8, 7 Hz).

EXAMPLE 12

A mixture of (3R,6R)-3-(3-aminopropyl)-6-(1-methylindol-3-ylmethyl)piperazine-2,5-dione (0.1 g) and acetic anhydride (0.08 g) in pyridine (1.0 ml) was heated at 100° C. for 1 hour. After the mixture was cooled to ambient temperature, the precipitated solid was collected by filtration and washed with pyridine (2 ml) and ethanol (5 ml) to give (3R,6R)-3-(3-acetamidopropyl)-6-(1-methylindol-3-ylmethyl)piperazine-2,5-dione (0.1 g).

mp: 138° C.

IR (Nujol): 3190, 1660 cm⁻¹.

NMR (DMSO-$d_6$) δ: 0.70 (3H, m), 1.00 (1H, m), 1.75 (3H, s), 2.40 (2H, m), 3.00 (1H, dd, J=13 Hz, 4.5 Hz), 3.22 (1H, dd, J=13 Hz, 4 Hz), 3.52 (1H, m), 3.74 (3H, s), 4.11 (1H, m), 7.05 (3H, m), 7.33 (1H, d, J=8 Hz), 7.58 (1H, d, J=8 Hz), 7.96 (1H, s), 8.05 (1H, s).

EXAMPLE 13

The following compound was prepared in a similar manner to that of Example 12.

(3S,6R)-3-(3-Acetamidopropyl)-6-(1-methylindol-3-ylmethyl)piperazine-2,5-dione mp: 124°–126° C.

IR (Nujol): 3280, 3180, 1670 cm⁻¹.

NMR (DMSO-$d_6$) δ: 1.30 (2H, m), 1.48 (2H, m), 1.75 (3H, s), 2.93 (2H, m), 3.10 (1H, m), 3.15 (1H, m), 3.22 (1H, m), 3.72 (3H, s), 4.05 (1H, m), 7.05 (3H, m), 7.35 (1H, d, J=8 Hz), 7.60 (1H, d, J=8 Hz), 7.75 (1H, m).

EXAMPLE 14

To a solution of (3R,6R)-3-(2-methylthioethyl)-6-[(R)-1-(1-naphthyl)ethyl]piperazine-2,5-dione (0.40 g) in dry dimethylformamide (40 ml) was added sodium hydride (116 mg). After the mixture was stirred at ambient temperature for 10 minutes, methyl iodide (0.19 ml) was added to the mixture. The reaction mixture was stirred for 5 minutes and the solvent was evaporated off under reduced pressure. The residue was extracted with chloroform (40 ml). The organic extract was washed with water, dried over magnesium sulfate, and evaporated in vacuo. The residue was chromatographed on silica gel (8 g) using a mixture of chloroform and methanol as eluent to give (3R,6R)-1,4-dimethyl-3-(2-methylthioethyl)-6-[(R)-1-(1-naphthyl)ethyl]piperazine-2,5-dione (0.16 g).

mp: 88°–90° C. (recrystallized from isopropyl ether).

IR (Chloroform): 1655 cm⁻¹.

NMR (CDCl₃) δ: 0.7–1.3 (2H, m), 1.63 (3H, d, J=6 Hz), 2.03 (3H, s), 2.50 (2H, t, J=6 Hz), 2.77 (3H, s), 2.80 (3H, s), 3.77 (1H, m), 4.30 (2H, m), 7.3–8.2 (7H, m).

EXAMPLE 15

The following compounds were prepared in a similar manner to that of Example 13.

(1) (3R,6R)-3-Butyl-1,4-dimethyl-6-[(R)-1-(1-naphthyl)ethyl]piperazine-2,5-dione mp: 71°–73° C.

IR (Nujol): 1650 cm⁻¹.

NMR (CDCl₃) δ: 0.88 (3H, m), 1.25 (6H, m), 1.63 (3H, d, J=7 Hz), 2.60 (3H, s), 2.83 (3H, s), 3.56 (1H, m), 4.23 (1H, m), 4.28 (1H, m), 7.4–8.2 (7H, m).

(2) (3R,6R)-3-Butyl-1,4-dimethyl-6-[(R)-1-(1-methylindol-3-yl)ethyl]piperazine-2,5-dione IR (Neat): 1650 cm⁻¹.

(3) (3R,6R)-1,4-Dimethyl-3-[(R)-1-(1-methylindol-3-yl)ethyl]-6-(2-methylthioethyl)piperazine-2,5-dione IR (CHCl$_3$): 1650 cm$^{-1}$.

(4) (3R,6R)-1,4-Dimethyl-3-[(S)-1-(1-methylindol-3-yl)ethyl]-6-(2-methylthioethyl)piperazine-2,5-dione
IR (CHCl$_3$): 1650 cm$^{-1}$.

EXAMPLE 16

A solution of (3R,6R)-3-(2-benzyloxycarbonylethyl)-6-(1-methylindol-3-ylmethyl)piperazine-2,5-dione (1.50 g) in ethanol (300 ml) containing 10% paradium on charcoal (0.75 g) was hydrogenated at ambient temperature and atmospheric pressure. After catalyst was filtered off and solvent was evaporated, crude solid was recrystallized from ethanol and dried in vacuo to give (3R,6R)-3-(2-carboxyethyl)-6-(1-methylindol-3-ylmethyl)piperazine-2,5-dione (0.58 g).

mp: 228° C.

IR (Nujol): 1720, 1660 cm$^{-1}$.

NMR (DMSO-d$_6$) δ: 1.14 (3H, m), 1.38 (1H, m), 2.98 (1H, dd, J=14, 4.5 Hz), 3.23 (1H, dd, J=14, 4 Hz), 3.63 (1H, m), 3.70 (3H, s), 4.12 (1H, m), 7.00 (3H, m), 7.28 (1H, d, J=8 Hz), 7.59 (1H, d, J=8 Hz), 7.97 (1H, s), 8.14 (1H, s).

EXAMPLE 17

| | |
|---|---|
| (3R,6R)-3-(2-Methylthioethyl)-6-[(R)-1-(1-naphthyl)ethyl]piperazine-2,5-dione | 500 (g) |
| Sucrose | 9000 |
| Hydroxypropylcellulose | 250 |
| Starch | 250 |

The above ingredients are blended and granulated or grained in a conventional manner into granules or small granules.

EXAMPLE 18

(1) To a solution of (αR,βR)-1,β-dimethyltryptophan methyl ester (6.36 g) and N$^α$-t-butoxycarbonyl-3-(2-pyridyl)-D-alanine (6.65 g) in dry methylene chloride (250 ml) was added dicyclohexylcarbodiimide (5.15 g), and resulting mixture was stirred for 1.5 hours at room temperature. After evaporation of the solvent, crude residue was taken up with ethyl acetate (200 ml), filtered, washed with water and saturated sodium bicarbonate solution, dried over magnesium sulfate, treated with active charcoal, and evaporated. N$^α$-[N-t-Butoxycarbonyl-3-(2-pyridyl)-D-alanyl]-1,β-dimethyl-D-tryptophan methyl ester (10.54 g) was obtained as an oil.

IR (Neat): 1715, 1695, 1670 cm$^{-1}$.

(2) A mixture of N$^α$-[N-t-butoxycarbonyl-3-(2-pyridyl)-D-alanyl]-1,β-dimethyl-D-tryptophan methyl ester (10.54 g) and trifluoroacetic acid (80 ml) was stirred on an ice bath for 30 minutes. After removal of the solvent, resultant crude residue was dissolved in ethanol (150 ml) and saturated ammonia in ethanol (150 ml) was added to the solution and resultant mixture was stirred for 16 hours at ambient temperature. After evaporation of the solvent, chloroform (200 ml) was added to the mixture. The insoluble material was filtered off and again solvent was evaporated in vacuo to give an oil which was chromatographed on silica gel (250 g, chloroform-methanol 20:1 as eluent) to afford (3R,6R)-3-[(R)-1-(1-methylindol-3-yl)ethyl]-6-(2-pyridylmethyl)piperazine-2,5-dione.

Crystallization from ethanol yielded 3.14 g of the crystals.

mp: 227°-228° C.

IR (Nujol): 3200, 1675, 1655 cm$^{-1}$.

EXAMPLE 19

The following compounds were prepared in a similar manner to that of Example 18(2).

(1) (3R,6RS)-3-(1-Methylindol-3-yl)methyl-6-(3-pyridylmethyl)piperazine-2,5-dione
mp: 231°-238° C.
IR (Nujol): 3200, 1670 cm$^{-1}$.

(2) (3R,6R)-3-(1-Methylindol-3-yl)methyl-6-(4-pyridylmethyl)piperazine-2,5-dione
mp: 263°-271° C.

(3) (3R,6R)-3-Butyl-6-(1-naphthylmethyl)piperazine-2,5-dione
mp: 249°-250° C.
IR (Nujol): 3190, 3040, 1670, 1660 cm$^{-1}$.

(4) (3R,6R)-3-[(R)-1-(1-Ethylindol-3-yl)ethyl]-6-(2-pyridylmethyl)piperazine-2,5-dione
mp: 237°-240° C.
IR (Nujol): 3200, 1675, 1660 cm$^{-1}$.

(5) (3R,6R)-3-[(R)-1-(5-Chloro-1-methylindol-3-yl)ethyl]-6-(2-pyridylmethyl)piperazine-2,5-dione
mp: 229°-234° C.
IR (Nujol): 3210, 1680, 1660 cm$^{-1}$.

(6) (3R,6R)-3-[(R)-1-(5-Methoxy-1-methylindol-3-yl)ethyl]-6-(2-pyridylmethyl)piperazine-2,5-dione
mp: 220°-222° C.
IR (CHCl$_3$): 3400, 1675 cm$^{-1}$.

(7) (3R,6R)-3-[(R)-1-(1-Methylindol-3-yl)ethyl]-6-(1,3-thiazol-4-ylmethyl)piperazine-2,5-dione
mp: 238°-241° C.
IR (CHCl$_3$): 3400, 1680 cm$^{-1}$.

EXAMPLE 20

(3R,6R)-3-[(R)-1-(1-Methylindol-3-yl)ethyl]-6-(2-pyridylmethyl)piperazine-2,5-dione (0.20 g) was dissolved in a mixture of ethanol (5 ml), chloroform (2 ml), and 1.4N ethanolic hydrogen chloride (0.5 ml) and solvent was evaporated in vacuo. The resultant crude residue was recrystallized from acetone to give hydrochloric acid salt of (3R,6R)-3-[(R)-1-(1-methylindol-3-yl)ethyl]-6-(2-pyridylmethyl)piperazine-2,5-dione (0.12 g).

mp: 180° C.

EXAMPLE 21

A mixture of (3R,6R)-3-[(R)-1-(1-methylindol-3-yl)ethyl]-6-(2-pyridylmethyl)piperazine-2,5-dione (0.10 g) and methyl iodide (5 ml) was stirred under reflux for 4 days. After evaporation of the excess methyl iodide, crude oily residue was washed with chloroform and ether, and dried in vacuo to give (3R,6R)-3-[(R)-1-(1-methylindol-3-yl)ethyl]-6-(1-methyl-2-pyridiniomethyl)piperazine-2,5-dione iodide as a solid (0.12 g).

NMR (DMSO-d$_6$, δ): 1.20 (1H, m), 1.45 (3H, d, J=7 Hz), 2.55 (1H, m), 3.70 (1H, m), 3.78 (3H, s), 3.81 (3H, s), 4.05 (2H, m), 5.95 (1H, d, J=8.5 Hz), 7.15 (3H, m), 7.40 (1H, d, J=8 Hz), 7.65 (1H, d, J=8 Hz), 7.73 (1H, d, J=1 Hz), 7.85 (1H, m), 8.13 (1H, m), 8.32 (1H, s), 8.80 (2H, m).

EXAMPLE 22

To a mixture of (3R,6R)-3-[(R)-1-(1-methylindol-3-yl)ethyl]-6-(1-methyl-2-pyridiniomethyl)piperazine-2,5-dione iodide (0.12 g), methanol (1.2 ml), and water (1.2 ml) was added sodium borohydride (0.12 g). The mixture was stirred on an ice bath for 1 hour, diluted with water (10 ml), and set aside in a refrigerator overnight. A precipitated solid was filtered, washed with water, and dried in vacuo to afford (3R,6R)-3-[(R)-1-methylindol-3-yl)ethyl]-6-[(RS)-1-methyl-1,2,3,6-tetrahydropyridin-6-yl-methyl]piperazine-2,5-dione (0.03 g).
mp: 235°–238° C.
IR (Nujol): 3200, 1670, 1660 cm⁻¹.

EXAMPLE 23

(1) To a solution of 5-chloro-1-ethylindole (6.17 g) and methyl (2R,3R)-N-benzyloxycarbonyl-3-methyl-2-aziridinecarboxylate (9.87 g) in dry methylene chloride (100 ml) which was cooled on an ice bath, was added boron trifluoride etherate (4 ml). The mixture was stirred for five minutes and washed with saturated sodium bicarbonate solution, treated with active charcoal, and dried over magnesium sulfate. After removal of the solvent, the crude residue was chromatographed on silica gel (100 g) (toluene as eluent) to give (αR,βR)-N-benzyloxycarbonyl-5-chloro-1-ethyl-β-methyltryptophan methyl ester (4.17 g) as an oil.
$[\alpha]_{20}^D -31.1°$ (in MeOH, C=1.3).

(2) A solution of (αR,βR)-Nα-Benzyloxycarbonyl-5-chloro-1-ethyl-β-methyltryptophan methyl ester (4.17 g) in methanol (100 ml) containing 10% paradium on charcoal (0.5 g) was hydrogenated. After removal of the catalyst and evaporation of the solvent, (αR,βR)-5-chloro-1-ethyl-β-methyltryptophan methyl ester (2.45 g) was obtained as a yellow amorphous powder.
$[\alpha]_{20}^D -37.1°$ (in MeOH, C=1.5).

(3) To a solution of (αR,βR)-5-chloro-1-ethyl-β-methyltryptophan methyl ester (1.24 g) and N-t-butoxycarbonyl-3-(2-pyridyl)-D-alanine (1.12 g) in dry methylene chloride (30 ml) which was cooled on an ice bath, was added a solution of N,N'-dicyclohexylcarbodiimide (0.9 g) in dry methylene chloride (5 ml). The mixture was stirred overnight at room temperature. After removal of the solvent, the crude residue was taken up with a mixture of ethyl acetate and water, filtered, and the organic layer was washed with saturated sodium bicarbonate solution, dried over magnesium sulfate, and solvent was evaporated off to give Nα-[N-t-butoxycarbonyl-3-(2-pyridyl)-D-alanyl](αR,βR)-5-chloro-1-ethyl-β-methyltryptophan methyl ester (2.29 g). To this compound was added trifluoroacetic acid (10 ml) and the mixture was stirred for 30 minutes on an ice bath. After evaporation of the solvent, the crude residue was dissolved in chloroform (50 ml), washed with saturated sodium bicarbonate solution, treated with active charcoal, dried over magnesium sulfate, and the solvent was evaporated off to give an oil (1.43 g). The crude material was dissolved in ethanol (10 ml) and saturated alcoholic ammonia (10 ml) was added. The resulting mixture was allowed to stand for 3 days at room temperature and concentrated in vacuo. The crude residue was chromatographed on silica gel (70 g) (chloroform and 50:1 mixture of chloroform and methanol as eluent) to give an oil (0.56 g) which was crystallized from ethanol to afford (3R,6R)-3-[(R)-1-(5-chloro-1-ethylindol-3-yl)ethyl]-6-(2-pyridylmethyl)piperazine-2,5-dione (0.34 g).
mp: 223°–226° C.
IR (Nujol): 3210, 1675, 1655 cm⁻¹.

EXAMPLE 24

(1) The following compound was prepared in a similar manner to that of Example 23(1).
(αR,βR)-N-Benzyloxycarbonyl-β-methyl-1-propyltryptophan methyl ether
$[\alpha]_{20}^D -22.4°$ (in MeOH, C=1.8).

(2) The following compound was prepared in a similar manner to that of Example 23(2).
(αR,βR)-β-Methyl-1-propyltryptophan methyl ester
$[\alpha]_{20}^D -26.4°$ (in MeOH, C=1.1).

(3) The following compound was prepared in a similar manner to that of Example 23(3).
(3R,6R)-3-[(R)-1-(1-Propylindol-3-yl)ethyl]-6-(2-pyridylmethyl)piperazine-2,5-dione
mp: 178°–181° C.
IR (Nujol): 1650 cm⁻¹.

(4) The following compound was prepared in a similar manner to that of Example 23(3)
(3R,6S)-3-[(R)-1-(1-propylindol-3-yl)ethyl]-6-(2-pyridylmethyl)piperazine-2,5-dione
mp: 175°–180° C.
IR (Nujol): 1670 cm⁻¹.

EXAMPLE 25

(1) The following compound was prepared in a similar manner to that of Example 23(1).
(αR,βR)-N-Benzyloxycarbonyl-1,β-dimethyl-5-fluorotryptophan methyl ester
$[\alpha]_{20}^D 32.5°$ (in MeOH, C=1.2).

(2) The following compound was prepared in a similar manner to that of Example 23(2).
(αR,βR)-1,β-Dimethyl-5-fluorotryptophan methyl ester
$[\alpha]_{20}^D -22.6°$ (in MeOH, C=0.4).

(3) The following compound was prepared in a similar manner to that of Example 23(3).
(3R,6R)-3-[(R)-1-(5-Fluoro-1-methylindol-3-yl)ethyl]-6-(2-pyridylmethyl)piperazine-2,5-dione
mp: 242°–248° C.
IR (Nujol): 1665 cm⁻¹.

EXAMPLE 26

The following compounds were prepared in a similar manner to that of Example 23(3).
(1) (3R,6S)-3-[(R)-1-(5-Fluoro-1-methylindol-3-yl)ethyl]-6-(2-pyridylmethyl)piperazine-2,5-dione
mp: 243°–248° C.
IR (Nujol): 1670 cm⁻¹.
(2) (3R,6S)-3-[(R)-1-(5-Chloro-1-ethylindol-3-yl)ethyl]-6-(2-pyridylmethyl)piperazine-2,5-dione
mp: 192°–194° C.
IR (Nujol): 1670 cm⁻¹.
(3) (3R,6R)-3-[(R)-1-(5-Chloro-1-ethylindol-3-yl)ethyl]-6-(4-thiazolylmethyl)piperazine-2,5-dione
mp: 190°–193° C.
IR (Nujol): 1670 cm⁻¹.
(4) (3R,6S)-3-[(R)-1-(5-Chloro-1-ethylindol-3-yl)ethyl]-6-(4-thiazolylmethyl)piperazine-2,5-dione
mp: 218°–220° C.
IR (Nujol): 1675 cm⁻¹.

EXAMPLE 27

(1) The following compound was prepared in a similar manner to that of Example 23(1).
(αR,βR)-N-Benzyloxycarbonyl-1-butyl-5-fluoro-β-methyltryptophan methyl ester
$[\alpha]_{20}^D -7.16°$ (in MeOH, C=1.65).

(2) The following compound was prepared in a similar manner to that of Example 23(2).
(αR,βR)-1-Butyl-5-fluoro-β-methyltryptophan methyl ester
$[\alpha]_{20}^D -7.99°$ (in MeOH, C=1.40).

(3) The following compound was prepared in a similar manner to that of Example 23(3).

(3R,6R)-3-[(R)-1-(1-Butyl-5-fluoroindol-3-yl)ethyl]-6-(2-pyridylmethyl)piperazine-2,5-dione
mp: 155°–160° C.
IR (Nujol): 1680 cm$^{-1}$.

EXAMPLE 28

The following compounds were prepared in a similar manner to that of Example 23(3).
(1) (3R,6S)-3-[(R)-1-(1-Butyl-5-fluoroindol-3-yl)ethyl]-6-(2-pyridylmethyl)piperazine-2,5-dione
mp: 173°–176° C.
IR (Nujol): 1665 cm$^{-1}$.
(2) (3R,6R)-3-[(R)-1-(1-Butyl-5-fluoroindol-3-yl)ethyl]-6-(4-thiazolylmethyl)piperazine-2,5-dione
mp: 180°–183° C.
IR (Nujol): 1670 cm$^{-1}$.

EXAMPLE 29

(1) The following compound was prepared in a similar manner to that of Example 23(1).
($\alpha$R,$\beta$R)-N-Benzyloxycarbonyl-1-butyl-5-chloro-2,$\beta$-dimethyltryptophan methyl ester.
$[\alpha]_{20}^D$ 2.72° (in MeOH, C=1.65).
(2) The following compound was prepared in a similar manner to that of Example 23(2).
($\alpha$R,$\beta$R)-5-Chloro-2,$\beta$-dimethyl-1-butyltryptophan methyl ester
$[\alpha]_{20}^D$ −1.06° (in MeOH, C=1.45).
(3) The following compound was prepared in a similar manner to that of Example 23(3).
(3R,6R)-3-[(R)-1-(1-Butyl-5-chloro-2-methylindol-3-yl)ethyl]-6-(2-pyridylmethyl)piperazine-2,5-dione
mp: 155°–168° C.
IR (Nujol): 1680 cm$^{-1}$.

EXAMPLE 30

The following compounds were prepared in a similar manner to that of Example 23(3).
(1) (3R,6S)-3-[(R)-1-(1-Butyl-5-chloro-2-methylindol-3-yl)ethyl]-6-(2-pyridylmethyl)piperazine-2,5-dione
mp: 183°–190° C.
IR (Nujol): 1660 cm$^{-1}$.
(2) (3R,6R)-3-[(R)-1-(1-Butyl-5-chloro-2-methylindol-3-yl)ethyl]-6-(4-thiazolylmethyl)piperazine-2,5-dione
mp: 105°–110° C.
IR (Nujol): 1670 cm$^{-1}$.

EXAMPLE 31

(1) The following compound was prepared in a similar to that of Example 23(1).
($\alpha$R,$\beta$R)-N-Benzyloxycarbonyl-5,$\beta$-dimethyl-1-propyltryptophan methyl ester
$[\alpha]_{20}^D$ −43.30° (in MeOH, C=0.86).
(2) The following compound was prepared in a similar manner to that of Example 23(2).
($\alpha$R,$\beta$R)-5,$\beta$-Dimethyl-1-propyltryptophan methyl ester
$[\alpha]_{20}^D$ −38.34° (in MeOH, C=1.15).
(3) The following compound was prepared in a similar manner to that of Example 23(3).
(3R,6R)-3-[(R)-1-(5-Methyl-1-propylindol-3-yl)ethyl]-6-(2-pyridylmethyl)piperazine-2,5-dione
mp: 214°–215° C.
IR (Nujol): 3200, 1665 cm$^{-1}$.

EXAMPLE 32

The following compounds were prepared in a similar manner to that of Example 23(3).
(1) (3R,6S)-3-[(R)-1-(5-Methyl-1-propylindol-3-yl)ethyl]-6-(2-pyridylmethyl)piperazine-2,5-dione
mp: 192°–193° C.
IR (Nujol): 3200, 1670 cm$^{-1}$.
(2) (3R,6R)-3-[(R)-1-(5-Methyl-1-propylindol-3-yl)ethyl]-6-(4-thiazolylmethyl)piperazine-2,5-dione
mp: 201.5°–202.5° C.
IR (Nujol): 3200, 1665 cm$^{-1}$.

EXAMPLE 33

(1) The following compound was prepared in a similar manner to that of Example 23(1).
($\alpha$R,$\beta$R)-N-Benzyloxycarbonyl-1-propyl-2,5,$\beta$-trimethyltryptophan methyl ester
$[\alpha]_{20}^D$ −1.45° (in MeOH, C=0.9).
(2) The following compound was prepared in a similar manner to that of Example 23(2).
($\alpha$R,$\beta$R)-1-Propyl-2,5,$\beta$-trimethyltryptophan methyl ester
$[\alpha]_{20}^D$ −0.71° (C=0.556 in MeOH).
(3) The following compound was prepared in a similar manner to that of Example 23(3).
(3R,6R)-3-[(R)-1-(2,5-Dimethyl-1-propylindol-3-yl)ethyl]-6-(2-pyridylmethyl)piperazine-2,5-dione
mp: 231.5°–232.0° C.
IR (Nujol): 3340, 3220, 3100, 1680, 1650 cm$^{-1}$.

EXAMPLE 34

The following compounds were prepared in a similar manner to that of Example 23(3).
(3R,6S)-3-[(R)-1-(2,5-Dimethyl-1-propylindol-3-yl)ethyl]-6-(2-pyridylmethyl)piperazine-2,5-dione
mp: 218.0° C.
IR (Nujol): 3200, 1665 cm$^{-1}$.

EXAMPLE 35

(1) The following compound was prepared in a similar manner to that of Example 23(1).
($\alpha$R,$\beta$R)-N-Benzyloxycarbonyl-1,2,$\beta$-trimethyltryptophan methyl ester
$[\alpha]_{20}^D$ −0.70° (in MeOH, C=1.7).
(2) The following compound was prepared in a similar manner to that of Example 23(2).
($\alpha$R,$\beta$R)-1,2,$\beta$-Trimethyltryptophan methyl ester
$[\alpha]_{20}^D$ −18.4° (in MeOH, C=1.0).
(3) The following compound was prepared in a similar manner to that of Example 23(3).
(3R,6R)-3-[(R)-1-(1,2-Dimethylindol-3-yl)ethyl]-6-(2-pyridylmethyl)piperazine-2,5-dione
mp: 265°–269° C.
IR (Nujol): 1675, 1650 cm$^{-1}$.

EXAMPLE 36

The following compound was prepared in a similar manner to that of Example 23(3).
(3R,6S)-3-[(R)-1-(1,2-Dimethylindol-3-yl)ethyl]-6-(2-pyridylmethyl)piperazine-2,5-dione
mp: 216°–219° C.
IR (Nujol): 1675 cm$^{-1}$.

EXAMPLE 37

(1) The following compound was prepared in a similar manner to that of Example 23(1).
($\alpha$R,$\beta$R)-N-Benzyloxycarbonyl-1,5,$\beta$-trimethyltryptophan methyl ether
$[\alpha]_{20}^D$ −19.2° (in MeOH, C=1.2).
(2) The following compound was prepared in a similar manner to that of Example 23(2).

(αR,βR)-1,5,β-Trimethyltryptophan methyl ester
[α]$_{20}^D$ −45.3° (in MeOH, C=1.2).
(3) The following compound was prepared in a similar manner to that of Example 23(3).
(3R,6R)-3-[(R)-1-(1,5-Dimethylindol-3-yl)ethyl]-6-(2-pyridylmethyl)piperazine-2,5-dione
mp: 256°–257° C.
IR (Nujol): 3200, 1650 cm$^{-1}$.

EXAMPLE 38

The following compound was prepared in a similar manner to that of Example 23(3).
(3R,6S)-3-[(R)-1-(1,5-Dimethylindol-3-yl)ethyl]-6-(2-pyridylmethyl)piperazine-2,5-dione
mp: 260°–262° C.
IR (Nujol): 3200, 1660 cm$^{-1}$.

EXAMPLE 39

(1) The following compound was prepared in a similar manner to that of Example 23(1).
(αR,βR)-N-Benzyloxycarbonyl-5-chloro-2,β-dimethyl-1-propyltryptophan methyl ester
[α]$_{20}^D$ 17.98° (in MeOH, C=1.3).
(2) The following compound was prepared in a similar manner to that of Example 23(2).
(αR,βR)-5-Chloro-2,β-dimethyl-1-propyltryptophan methyl ester
[α]$_{20}^D$ −0.50° (in MeOH, C=1.0).
(3) The following compound was prepared in a similar manner to that of Example 23(3).
(3R,6R)-3-[(R)-1-(5-Chloro-2-methyl-1-propylindol-3-yl)ethyl]-6-(2-pyridylmethyl)piperazine-2,5-dione
mp: 195° C.
IR (Nujol): 1660 cm$^{-1}$.

EXAMPLE 40

The following compounds were prepared in a similar manner to that of Example 23(3).
(1) (3R,6S)-3-[(R)-1-(5-Chloro-2-methyl-1-propylindol-3-yl)ethyl]-6-(2-pyridylmethyl)piperazine-2,5-dione
mp: 197°–198° C.
IR (Nujol): 1670 cm$^{-1}$.
(2) (3R,6R)-3-[(R)-1-(5-Chloro-2-methyl-1-propylindol-3-yl)ethyl]6-(4-thiazolylmethyl)piperazine-2,5-dione
mp: 160° C.
IR (Nujol): 1660 cm$^{-1}$.

EXAMPLE 41

(1) The following compound was prepared in a similar manner to that of Example 23(1).
(αR,βR)-N-Benzyloxycarbonyl-1-butyl-2,β-dimethyltryptophan methyl ester
[α]$_{20}^D$ −3.27° (in MeOH, C=1.365).
(2) The following compound was prepared in a similar manner to that of Example 23(2).
(αR,βR)-1-Butyl-2,β-dimethyltryptophan methyl ester
[α]$_{20}^D$ −7.21° (in MeOH, C=1.065).
(3) The following compound was prepared in a similar manner to that of Example 23(3).
(3R,6R)-3-[(R)-1-(1-Butyl-2-methylindol-3-yl)ethyl]-6-(4-thiazolylmethyl)piperazine-2,5-dione
mp: 200°–201° C.
IR (CHCl$_3$): 1680 cm$^{-1}$.

EXAMPLE 42

The following compounds were prepared in a similar manner to that of Example 23(3).
(1) (3R,6R)-3-[(R)-1-(1-Butyl-2-methylindol-3-yl)ethyl]-6-(2-pyridylmethyl)piperazine-2,5-dione
mp: 210°–210.5° C.
IR (CHCl$_3$): 1677 cm$^{-1}$.
(2) (3R,6S)-3-[(R)-1-(1-Butyl-2-methylindol-3-yl)ethyl]-6-(2-pyridylmethyl)piperazine-2,5-dione
mp: 150° C.
IR (CHCl$_3$): 1680 cm$^{-1}$.

EXAMPLE 43

(1) The following compound was prepared in a similar manner to that of Example 23(1).
(αR,βR)-N-Benzyloxycarbonyl-β-methyl-1-isobutyltryptophan methyl ester
[α]$_{20}^D$ −33.14 (in MeOH, C=1.095).
(2) The following compound was prepared in a similar manner to that of Example 23(2).
(αR,βR)-β-Methyl-1-isobutyltryptophan methyl ester
[α]$_{20}^D$ −33.19 (in MeOH, C=1.03).
(3) The following compound was prepared in a similar manner to that of Example 23(3).
(3R,6R)-3-[(R)-1-(1-Isobutylindol-3-yl)ethyl]-6-(2-pyridylmethyl)piperazine-2,5-dione
mp: 204° C.
IR (CHCl$_3$): 1678 cm$^{-1}$.

EXAMPLE 44

The following compounds were prepared in a similar manner to that of Example 23(3).
(1) (3R,6S)-3-[(R)-1-(1-Isobutylindol-3-yl)ethyl]-6-(2-pyridylmethyl)piperazine-2,5-dione
mp: 232° C.
IR (CHCl$_3$): 1680 cm$^{-1}$.
(2) (3R,6R)-3-[(R)-1-(1-Isobutylindol-3-yl)ethyl]-6-(4-thiazolylmethyl)piperazine-2,5-dione
mp: 126°–127.5° C.
IR (CHCl$_3$): 1679 cm$^{-1}$.

EXAMPLE 45

(1) To a solution of (αR,βR)-N-benzyloxycarbonyl-1,β-dimethyltryptphan methyl ester (6.0 g) in methanol (60 ml) was added a solution of sodium hydroxide (1.26 g) in water (10 ml), and the resulting mixture was stirred at room temperature for 8 hours. The reaction mixture was acidified with 10% hydrochloric acid, concentrated to a volume of 30 ml, extracted with ethyl acetate (30 ml×2). Combined organic extracts were washed with water, dried over magnesium sulfate, treated with active charcoal, and evaporated in vacuo to give (αR,βR)-N-benzyloxycarbonyl-1,β-dimethyltryptophan (5.29 g) as an oil.
[α]$_{20}^D$ −32.4° (in MeOH, C=1.2).
(2) A mixture of (αR,βR)-N-benzyloxycarbonyl-1,β-dimethyltryptophan (1.95 g), N,N'-disuccinimidyl carbonate (1.5 g), and pyridine (0.46 g) in dry acetonitrile (15 ml) was stirred at room temperature for 18 hours. After evaporation of the solvent, the residue was dissolved in ethyl acetate (30 ml), washed with water (10 ml), 10% hydrochloric acid (10 ml), water (5 ml), saturated sodium bicarbonate solution (10 ml), and saturated sodium chloride solution (5 ml), dried over magnesium sulfate, and evaporated in vacuo to give an oil (3.38 g). The residual oil (3.38 g) and 3-(2-pyridyl)-D-alanine ethyl ester dihydrochloride (1.56 g) were dissolved in a mixture of dioxane (30 ml) and water (15 ml). The mixture was neutralized with triethylamine (1.78 g) and stirred at room temperature overnight. After evaporation of the solvent, the reaction mixture was extracted with ethyl acetate (30 ml×2). The combined organic extract was washed with water, saturated sodium bicarbonate solution, and saturated sodium chloride solution dried over magnesium sulfate, and evaporated in vacuo to give $N^\alpha$-[($\alpha$R,$\beta$R)-N-benzyloxycarbonyl-1,$\beta$-dimethyltryptophyl]-3-(2-pyridyl)-D-alanine ethyl ester (2.78 g). The resultant compound in methanol (28 ml) was hydrogenated over 10% paradium-charcoal (0.28 g) to give an oil (2.05 g), which was dissolved in ethanol (10 ml) and saturated ammonia-ethanol solution (10 ml) was added. The mixture was allowed to stand at room temperature for 18 hours and solvent was evaporated in vacuo. Crude residue was washed with ethyl acetate to give crystals (1.40 g). The crystals was recrystallized from ethanol to give (3R,6R)-3-[(R)-1-(1-methylindol-3-yl)ethyl]-6-(2-pyridylmethyl)piperazine-2,5-dione (1.24 g).

Physicochemical properties of this compound were identical with that of the object compound of Example 18.

EXAMPLE 46

The following compounds were prepared in a similar manner to that of Example 45(2).
(1) (3R,6R)-3-[(R)-1-(1-Methylindol-3-yl)ethyl]-6-(2-quinolylmethyl)piperazine-2,5-dione
mp: 261°–267° C.
IR (Nujol): 3190, 1670, 1655 cm$^{-1}$.
(2) (3R,6S)-3-[(R)-1-(1-Methylindol-3-yl)ethyl]-6-(2-quinolylmethyl)piperazine-2,5-dione
mp: 211°–218° C.
IR (Nujol): 3190, 1670 cm$^{-1}$.

EXAMPLE 47

(1) The following compound was prepared in a similar manner to that of Example 23(1).
($\alpha$R,$\beta$R)-N-Benzyloxycarbonyl-1,$\beta$-dimethyl-2-phenyltryptophan methyl ester
$[\alpha]_{20}{}^D$ −0.86° (in MeOH, C=1.5).
(2) The following compound was prepared in a similar manner to that of Example 23(2).
($\alpha$R,$\beta$R)-1,$\beta$-Dimethyl-2-phenyltryptophan methyl ester
$[\alpha]_{20}{}^D$ 18.1° (in MeOH, C=1.1).
(3) The following compounds were prepared in a similar manner to that of Example 23(3).
(a) (3R,6R)-3-[(R)-1-(1-Methyl-2-phenylindol-3-yl)ethyl]-6-(2-pyridylmethyl)piperazine-2,5-dione
mp: 233°–236° C.
IR (Nujol): 1680 cm$^{-1}$.
(b) (3R,6S)-3-[(R)-1-(1-Methyl-2-phenylindol-3-yl)ethyl]-6-(2-pyridylmethyl)piperazine-2,5-dione
mp: 222°–223° C.
IR (Nujol): 1675 cm$^{-1}$.

EXAMPLE 48

(3R,6R)-3-[(R)-1-(1-Methylindol-3-yl)ethyl]-6-(2-pyridylmethyl)piperazine-2,5-dione (5.0 g) was dissolved in water (10 ml) containing sulfuric acid (1.40 g). After evaporation of the water, crude residue was recrystallized from ethanol to give sulfuric acid salt of (3R,6R)-3-[(R)-1-(1-methylindol-3-yl)ethyl]-6-(2-pyridylmethyl)piperazine-2,5-dione (3.32 g).
mp: 139° C.

EXAMPLE 49

(3R,6R)-3-[(R)-1-(1-Methylindole-3-yl)ethyl]-6-(2-pyridylmethyl)piperazine-2,5-dione (5 g) was dissolved in water (10 ml) containing oxalic acid (1.91 g). After evaporation of the water, crude solid was recrystallized from ethanol to give oxalic acid salt of (3R,6R)-3-[(R)-1-(1-methylindol-3-yl)ethyl]-6-(2-pyridylmethyl)piperazine-2,5-dione (5.67 g).
mp: 170°–173° C.

EXAMPLE 50

(1) The following compound was prepared in a similar manner to that of Example 45(1).
($\alpha$R,$\beta$R)-N-t-Butoxycarbonyl-5-bromo-1-ethyl-$\beta$-methyltryptophan
$[\alpha]_{20}{}^D$ −41.2° (in MeOH, c=1.2).
(2) The following compound was prepared in a similar manner to that of Example 45 (2)
(3R,6R)-3-[(R)-1-(5-Bromo-1-ethylindol-3-yl)ethyl]-6-(2-pyridylmethyl)piperazine-2,5-dione
mp: 232°–233° C.
IR(Nujol): 1645 cm$^{-1}$.

EXAMPLE 51

(1) The following compound was prepared in a similar manner to that of Example 45(1).
($\alpha$R,$\beta$R)-N-t-Butoxycarbonyl-1-ethyl-5-methoxy-$\beta$-methyltryptophan
$[\alpha]_{20}{}^D$ −29.3° (in MeOH, c=1.1).
(2) The following compound was prepared in a similar manner to that of Example 45(2).
(3R,6R)-3-[(R)-1-(1-Ethyl-5-methoxyindol-3-yl)ethyl]-6-(2-pyridylmethyl)piperazine-2,5-dione
mp: 201°–203° C.
IR(Nujol): 1650 cm$^{-1}$.

EXAMPLE 52

(1) The following compound was prepared in a similar manner to that of Example 45(1).
($\alpha$R,$\beta$R)-N-t-Butoxycarbonyl-1-methyl-$\beta$-phenyltryptophan
IR(CHCl$_3$): 1720 cm$^{-1}$.
(2) The following compound was prepared in a similar manner to that of Example 45(2).
(3R,6R)-3-[(R)-$\alpha$-(1-Methylindol-3-yl)benzyl]-6-(2-pyridylmethyl)piperazine-2,5-dione
mp: 238°–240° C.

EXAMPLE 53

The following compound was prepared in a similar manner to that of Example 45(2).
(3R,6S)-3-[(R)-$\alpha$-(1-Methylindol-3-yl)benzyl]-6-(2-pyridylmethyl)piperazine-2,5-dione
mp: 265°–268° C.

EXAMPLE 54

(1) The following compound was prepared in a similar manner to that of Example 45(1).
($\alpha$R,$\beta$R)-N-t-Butoxycarbonyl-5-benzyloxy-1-ethyl-$\beta$-methyltryptophan
$[\alpha]_{20}{}^D$ −52.4° (in MeOH, c=1.8).
(2) The following compound was prepared in a similar manner to that of Example 45(2).
(3R,6R)-3-[(R)-1-(5-Benzyloxy-1-ethylindol-3-yl)ethyl]-6-(2-pyridylmethyl)piperazine-2,5-dione
mp: 243°–246° C.
IR(Nujol): 1660, 1640 cm$^{-1}$.

EXAMPLE 55

The following compound was prepared in a similar manner to that of Example 45 (2).

(3R,6S)-3-[(R)-1-(5-Benzyloxy-1-ethylindol-3-yl)ethyl]-6-(2-pyridylmethyl)piperazine-2,5-dione
mp: 195°–196° C.
IR(Nujol): 1670, 1650 cm$^{-1}$.

EXAMPLE 56

(1) The following compound was prepared in a similar manner to that of Example 45 (1).
(αR,βR)-N-t-Butoxycarbonyl-β-ethyl-1-methyltryptophan
IR(neat): 1720 cm$^{-1}$.

(2) The following compound was prepared in a similar manner to that of Example 45(2).
(3R,6R)-3-[(R)-1-Methylindol-3-yl)propyl]-6-(2-pyridylmethyl)piperazine-2,5-dione
mp: 217°–219° C.
IR(Nujol): 1680 cm$^{-1}$.

EXAMPLE 57

(1) The following compound was prepared in a similar manner to that of Example 45 (1).
(αR,βR)-N-Benzyloxycarbonyl-6,β-dimethyl-1-ethyltryptophan
$[\alpha]_{20}^{D}$ –30.3° (in MeOH, c=1.3).
IR(neat): 1700 cm$^{-1}$.

(2) The following compound was prepared in a similar manner to that of Example 45(2).
(3R,6R)-3-[(R)-1-(1-Ethyl-6-methylindol-3-yl)ethyl]-6-(2-pyridylmethyl)piperazine-2,5-dione
mp: 216°–217° C.
IR(Nujol): 1660, 1650 cm$^{-1}$.

EXAMPLE 58

The following compound was prepared in a similar manner to that of Example 45(2).
(3R,6R)-3-[(R)-1-(1-Ethyl-6-methylindol-3-yl)ethyl]-6-(4-thiazolylmethyl)piperazine-2,5-dione
mp: 229°–230° C.

EXAMPLE 59

(1) The following compound was prepared in a similar manner to that of Example 45 (1).
(αR,βR)-N-Benzyloxycarbonyl-5,β-dimethyl-1-ethyltryptophan
$[\alpha]_{20}^{D}$ –34.7° (in MeOH, c=1.7).

(2) The following compound was prepared in a similar manner to that of Example 45 (2).
(3R,6R)-3-[(R)-1-(1-Ethyl-5-methylindol-3-yl)ethyl]-6-(2-pyridylmethyl)piperazine-2,5-dione
mp: 212° C.
IR(Nujol): 1650 cm$^{-1}$.

(3) The following compound was prepared in a similar manner to that of Example 48.
Hydrochloric acid salt of (3R,6R)-3-[(R)-1-(1-Ethyl-5-methylindol-3-yl)ethyl]-6-(2-pyridylmethyl)piperazine-2,5-dione
mp: 135° C.
IR(Nujol): 1670, 1640 cm$^{-1}$.

EXAMPLE 60

(1) To a stirred suspension of sodium hydride (60%, 2.10 g) in dry tetrahydrofuran (30 ml) was added a solution of (αR,βR)-N-t-butoxycarbonyl-5-chloro-1-ethyl-β-methyltryptophan (5.0 g) in dry tetrahydrofuran (20 ml) under nitrogen atmosphere on an ice bath. The resulting mixture was stirred at room temperature for 1 hour and methyl iodide (3.28 ml) was added to the mixture. After additional stirring overnight, the reaction mixture was poured into water, washed with ether, acidified with .1N hydrochloric acid, and extracted with ethyl acetate to give
(αR,βR)-N-t-butoxycarbonyl-5-chloro-1-ethyl-N$^\alpha$,β-dimethyltryptophan as an oil (4.8 g)
IR(neat): 1720 cm$^{-1}$.

(2) The following compound was prepared in a similar manner to that of Example 45 (2).
(3R,6R)-3-[(R)-1-(5-Chloro-1-ethylindol-3-yl)ethyl]-4-methyl-6-(2-pyridylmethyl)piperazine-2,5-dione
mp: 173°–178° C.
IR(Nujol): 1660, 1680 cm$^{-1}$.

EXAMPLE 61

A solution of methanesulfonic acid (187.5 g) in 98% aqueous ethanol (7 l) was heated to 60° C. under stream of nitrogen. (3R,6R)-3-[(R)-1-(1-methylindol-3-yl)ethyl]-6-(2-pyridylmethyl)piperazine-2,5-dione (699.1 g) was added to the solution. After the mixture was stirred for 10 minutes, the mixture was allowed to stand for 20 hours at room temperature. The precipitated crystalline solid was collected by filtration and washed with absolute ethanol (1 l) to give methanesulfonic acid salt of (3R,6R)-3-[(R)-1-(1-methylindol-3-yl)ethyl]-6-(2-pyridylmethyl)piperazine-2,5-dione (708.4 g).
m.p. 221°~224° C.

We claim:
1. A method for the prevention and treatment of diseases caused by platelet activating factor, comprising:
administering to a subject a therapeutically effective amount of a piperazine compound of the formula:

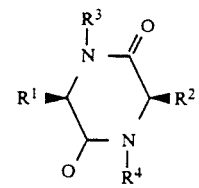

wherein R$^1$ is aryl, ar(lower)alkyl which may have lower alkoxy, indolyl(lower)alkyl, benzothienyl(lower-)alkyl, quinolyl(lower)alkyl, pyridyl(lower)alkyl, thiazolyl(lower)alkyl, N-loweralkylindolyl(lower)alkyl, N-loweralkyltetrahydropyridyl(lower)alkyl, N-loweralkylindolyl(lower)alkyl having a phenyl group on the indole ring, or a group of the formula:

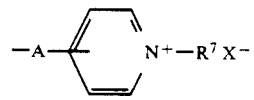

wherein
A is lower alkylene, R$^7$ is lower alkyl and X is a halide;
R$^2$ is C$_{1-22}$ alkyl, lower alkylthio(lower)alkyl, lower alkenylthio(lower)alkyl, hydroxy(lower)alkyl, lower alkanoyloxy or ar(lower)alkoxy protected hydroxy(lower)alkyl, amino(lower)alkyl, lower alkanoyl, aroyl, or ar(lower)alkoxycarbonyl protected amino(lower)alkyl, carboxy(lower)alkyl, lower alkoxycarbonyl or ar(lower)alkoxycarbonyl protected carboxy(lower)alkyl, arylthio(lower)alkyl, ar(lower)alkylthio(lower)alkyl, N-loweralkylindolyl(lower)alkyl, N-loweralkylindolyl(lower)alkyl having 1 or 2 lower alkyl groups on the indole ring, N-lower alkylindolyl(lower)alkyl having halogen substitution on the indole ring, N-lower alkylindolyl(lower)alkyl having lower alkyl and halogen substitution on the indole ring, N-lower alkyl indole(lower)alkyl having lower alkoxy substitution on the indole ring, N-loweralkylindolyl(lower)alkyl having phenyl substitution on the indole ring, N-loweralkylindolyl(lower)alkyl substituted by phenyl(lower)alkoxy on the indole ring, substituted by phenyl-disubstituted lower alkyl, or N-lower alkylindolyl- and phenyl-disubstituted lower alkyl; and $R^3$ and $R^4$ are each hydrogen or lower alkyl; or a pharmaceutically acceptable salt thereof.

* * * * *